US010030257B2

(12) United States Patent
Brune et al.

(10) Patent No.: US 10,030,257 B2
(45) Date of Patent: *Jul. 24, 2018

(54) SEPARATOME-BASED PROTEIN EXPRESSION AND PURIFICATION PLATFORM

(71) Applicants: BOARD OF TRUSTEES OF THE UNIVERSITY OF ARKANSAS, Little Rock, AR (US); UNIVERSITY OF PITTSBURGH—OF THE COMMONWEALTH SYSTEM OF HIGHER EDUCATION, Pittsburgh, PA (US)

(72) Inventors: Ellen M. Brune, Fayetteville, AR (US); Robert R. Beitle, Jr., Fayetteville, AR (US); Mohammad M. Ataai, Pittsburgh, PA (US); Patrick R. Bartlow, Pittsburgh, PA (US); Ralph L. Henry, Fayetteville, AR (US)

(73) Assignees: BOARD OF TRUSTEES OF THE UNIVERSITY OF ARKANSAS, Little Rock, AR (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,220

(22) Filed: Feb. 9, 2017

(65) Prior Publication Data
US 2017/0218422 A1 Aug. 3, 2017

Related U.S. Application Data

(63) Continuation of application No. 14/521,845, filed on Oct. 23, 2014, now Pat. No. 9,816,068, which is a continuation of application No. 14/056,747, filed on Oct. 17, 2013, now Pat. No. 8,927,231, which is a continuation of application No. PCT/US2013/030549, filed on Mar. 12, 2013.

(60) Provisional application No. 61/610,298, filed on Mar. 13, 2012.

(51) Int. Cl.
| | |
|---|---|
| C12P 21/00 | (2006.01) |
| C12N 1/20 | (2006.01) |
| C12N 9/00 | (2006.01) |
| B01D 15/38 | (2006.01) |
| B01D 15/42 | (2006.01) |
| B01D 15/20 | (2006.01) |
| B01D 15/36 | (2006.01) |
| C12N 5/07 | (2010.01) |
| C12N 15/09 | (2006.01) |

(52) U.S. Cl.
CPC ............ *C12P 21/00* (2013.01); *B01D 15/203* (2013.01); *B01D 15/362* (2013.01); *B01D 15/363* (2013.01); *B01D 15/3804* (2013.01); *B01D 15/424* (2013.01); *C12N 1/20* (2013.01); *C12N 9/00* (2013.01)

(58) Field of Classification Search
None
See application file for complete search history.

(56) References Cited

U.S. PATENT DOCUMENTS

| | | | |
|---|---|---|---|
| 6,989,265 B2 | 1/2006 | Blattner et al. | |
| 7,303,906 B2 | 12/2007 | Blattner et al. | |
| 8,039,243 B2 | 10/2011 | Blattner et al. | |
| 8,043,842 B2 | 10/2011 | Blattner et al. | |
| 8,119,365 B2 | 2/2012 | Blattner et al. | |
| 8,178,339 B2 | 5/2012 | Campbell et al. | |
| 8,697,359 B1 | 4/2014 | Zhang | |

(Continued)

FOREIGN PATENT DOCUMENTS

| | | |
|---|---|---|
| EP | 1483367 B1 | 5/2010 |
| JP | 2007306910 A | 11/2007 |

(Continued)

OTHER PUBLICATIONS

Communication from the European Patent Office in non-counterpart European Patent Application EP14846151.0, dated Mar. 8, 2017 (8 pages total).
Liu et al. (2009) "Use of proteomics for design of a tailored host cell for highly efficient protein purification", J. Chromatog. A 1216(12):2433-2438.
Tiwari et al. (2010) "Identification and characterization of native proteins of *Escherichia coli* BL-21 that display affinity towards Immobilized Metal Affinity Chromatography and Hydrophobic Interaction Chromatography Matrices", Protein Expression and Purification 70(2):191-195.

(Continued)

*Primary Examiner* — Nancy J Leith
(74) *Attorney, Agent, or Firm* — Charles E. Cohen

(57) ABSTRACT

Provided is a separatome-based recombinant peptide, polypeptide, and protein expression and purification platform based on the juxtaposition of the binding properties of host cell genomic peptides, polypeptides, and proteins with the characteristics and location of the corresponding genes on the host cell chromosome, such as that of *E. coli*, yeast, *Bacillus subtilis* or other prokaryotes, insect cells, mammalian cells, etc. The separatome-based protein expression and purification platform quantitatively describes and identifies priority deletions, modifications, or inhibitions of certain gene products to increase chromatographic separation efficiency, defined as an increase in column capacity, column selectivity, or both. Moreover, the separatome-based protein expression and purification platform provides a computerized knowledge tool that, given separatome data and a target recombinant peptide, polypeptide, or protein, intuitively suggests strategies leading to efficient product purification. The separatome-based protein expression and purification platform is an efficient bioseparation system that intertwines host cell expression systems and chromatography.

27 Claims, 5 Drawing Sheets

(56) References Cited

U.S. PATENT DOCUMENTS

| | | |
|---|---|---|
| 8,927,231 B2 | 1/2015 | Brune et al. |
| 2005/0136449 A1 | 6/2005 | Hanson et al. |
| 2009/0075333 A1 | 3/2009 | Campbell et al. |
| 2009/0075352 A1 | 3/2009 | Lee et al. |
| 2012/0183995 A1 | 7/2012 | Ferrari et al. |
| 2012/0219994 A1 | 8/2012 | Blattner et al. |
| 2015/0139944 A1 | 5/2015 | Brune et al. |
| 2016/0230177 A1 | 8/2016 | Brune et al. |

FOREIGN PATENT DOCUMENTS

| | | |
|---|---|---|
| WO | 2012033653 A1 | 3/2012 |
| WO | 2013138351 A1 | 9/2013 |

OTHER PUBLICATIONS

Communication from the European Patent Office in counterpart European Patent Application EP13714069.5, dated Mar. 24, 2017 (12 pages total).
First Official Action from the Canadian Intellectual Property Office in non-counterpart Canadian Patent Application No. 2,924,650, dated Mar. 31, 2017 (4 pages total).
Yu et al. (2002) "Minimization of the *Escherichia coli* genome using a Tn5-targeted Cre/loxP excision system", Nature Biotechnol. 20:1018-1023.
Asenjo et al. (2004) "Is there a rational method to purify proteins? From expert systems to proteomics", Journal of Molecular Recognition 17:236-247.
Cai et al. (2004) "Genomic Data for Alternate Production Strategies. I. Identification of Major Contaminating Species for Cobalt+2 Immobilized Metal Affinity Chromatography", Biotechnol. Bioeng. 88(1):77-83.
Communication from the European Patent Office in connection with the examination of counterpart European Patent Application Publication No. EP13714069.5, dated Sep. 7, 2016 (10 pages).
Communication from the European Patent Office in connection with the examination of counterpart European Patent Application Publication No. EP13714069.5, dated Jan. 14, 2016 (6 pages).
Bartlow et al. (2011a) "Identification of native *Escherichia coli* BL21 (DE3) proteins that bind to immobilized metal affinity chromatography under high imidazole conditions and use of 2D-DIGE to evaluate contamination pools with respect to recombinant protein expression level", Protein Expression and Purification 78:216-224.
Bartlow et al. (2011b) "Evaluation of *Escherichia coli* Proteins that Burden Nonaffinity-Based Chromatography as a Potential Strategy for Improved Purification Performance", American Institute of Chemical Engineers Biotechnol. Prog. 28(1):137-145.
Caparon et al. (2009) "Integrated Solution to Purification Challenges in the Manufacture of a Soluble Recombinant Protein in *E. coli*", Biotechnol. Bioeng. 105(2):239 -249.
Conrad et al. (2010) "RNA polymerase mutants found through adaptive evolution reprogram *Escherichia coli* for optimal growth in minimal media", Proc. Natl. Acad. Sci. USA 107(47):20500-20505.
Song et al. (2009) "Bioinformatic Comparison of Bacterial Secretomes", Genomics Proteomics Bioinformatics 7(1-2):37-46.
PCT International Search Report and Written Opinion of the International Searching Authority in PCT/US2013/030549 (dated Aug. 7, 2013).
Brune et al. (Jan. 21, 2013) Cambridge Healthtech Institute (CHI) Oral Abstract entitled "Genetic Engineering of *E. coli* to Facilitate Downstream Purification".
Brune et al. (Jan. 21, 2013) Cambridge Healthtech Institute (CHI) Peptalk Oral Presentation entitled "Genetic Engineering of *E. coli* to Facilitate Downstream Purification".
Brune et al. (Jan. 21, 2013) Cambridge Healthtech Institute (CHI) Peptalk Poster Abstract entitled "Genetic Engineering of *E. coli* to Facilitate Downstream Purification".
Brune et al. (Jan. 21, 2013) Cambridge Healthtech Institute (CHI) Peptalk Poster entitled "Genetic Engineering of *E. coli* to Facilitate Downstream Purification".
Beitle et al. (Oct. 23, 2012) Arkansas Biosciences Institute Oral Presentation entitled "Proteome-driven efficient bioseparation by rewriting the host cell genome".
E. Brune (Oct. 20, 2011) AIChE Annual Meeting Oral Presentation entitled "Proteome-Based Development of Affinity Motifs and Reduced Contaminant Strains".
E. Brune (Dec. 5, 2012) Dept. of Defense Threat Reduction Agency (DTRA) TechWatch Oral Presentation entitled "An *Escherichia coli* platform for biotherapeutics based on robust, separation-friendly strains".
E. Brune (Dec. 5, 2012) Dept. of Defense Threat Reduction Agency (DTRA) Abstract entitled "Development of a recombinant protein expression platform: Simplifying purification through genomic modifications".
Bartlow et al. (Fall, 2008) American Chemical Society Presentation entitled "Design of recombinant strains based on host cell elution profiles".
Bartlow et al. (Nov. 8-13, 2009) AIChE 2009 Annual Fall Scientific Meeting Presentation entitled "Knockout and Mutational Tailoring of Host Strains to Simplify Bioseparation".
Bartlow et al. (Oct. 19, 2011) AIChE Annual Meeting Presentation entitled "Evaluation of *Escherichia coli* Proteins that Burden Recombinant Protein Purification on Inexpensive, Non-Affinity-Based Resins".
Haley et al. (Nov. 2, 2005) AIChE Annual Meeting Abstract entitled "Circumventing the Effects of High Binding Immobilized Metal Affinity Chromatography Contaminants".
Varakala et al. (Nov. 2, 2005) AIChE Annual Meeting Abstract entitled "Improvement Upon Bioseparation by Altering the Host Genome".
Beitle et al. (Nov. 15, 2006) AIChE Annual Meeting Abstract entitled "A Rational Method to Improve Bioseparation Via Proteomics".
Varakala et al. (Nov. 7, 2007) AIChE Annual Meeting Abstract entitled "The Metalloproteome of *Escherichia coli*: Its Application in Downstream Processing Via Imac".
Bartlow et al. (Oct. 19, 2011) AIChE Annual Meeting Abstract entitled "Evaluation of *Escherichia coli* Proteins That Burden Recombinant Protein Purification on Inexpensive, Non-Affinity-Based Resins".
Brune et al. (Oct. 20, 2011) AIChE Annual Meeting Abstract entitled "Proteome-Based Development of Affinity Motifs and Reduced Contaminant Strains".
R. Varakala (May 2008) Ph.D. Dissertation, University of Arkansas, entitled "Proteome Based Improvements for Immobilized Metal Affinity Chromatography in an *Escherichia coli* Expression System".
Brune et al. (Mar. 27, 2011) 41st ACS National Meeting & Exposition, Poster Presentation entitled "Novel Affinity Tails, Based on Genomic Data, for Immobilized Metal Affinity and Ion-Exchange Chromatographies".
Brune et al. (Jan. 11, 2011) Cambridge Healthtech Institute (CHI) Peptalk Poster Presentation entitled "Development of Next-Generation Affinity Sequences for Use With Both Immobilized Metal Affinity Chromatography and Ion Exchange Chromatography".
Brune et al. (Mar. 27, 2011) 41st ACS National Meeting & Exposition, Abstract for Poster entitled "Novel Affinity Tails, Based on Genomic Data, for Immobilized Metal Affinity and Ion-Exchange Chromatographies".
Brune et al. (Jan. 11, 2011) Cambridge Healthtech Institute (CHI) Peptalk Abstract for Poster entitled "Development of Next-Generation Affinity Sequences for Use With Both Immobilized Metal Affinity Chromatography and Ion Exchange Chromatography".
Jun-Ichi Kato et al. (2007) Construction of consecutive deletions of the *Escherichia coli* chromosome, Molecular Systems Biology 3: Article No. 132:1-7.
Jun-Ichi Kato et al. (2008) "Construction of Long Chromosomal Deletion Mutants of *Escherichia coli* and Minizimation of the Genome", Meth. Mol. Biol., vol. 416: Microbial Gene Essentiality, Humana Press, NJ, pp. 279-293.

(56) References Cited

OTHER PUBLICATIONS

Hashimoto et al. (2005) "Cell size and nucleoid organization of engineered *Escherichia coli* cells with a reduced genome", Molecular Microbiology 55(1):137-149.
Lee et al. (2005) "Metabolic Engineering of *Escherichia coli* for Enhanced Production of Succinic Acid, Based on Genome Comparison and In Silico Gene Knockout Simulation", Applied and Environmental Microbiology 71(12):7880-7887.
Ellen M. Brune, Ph.D. Dissertation entitled "Bacterial Strains Based on the Separatome of *Escherichia coli*", May 2013, University of Arkansas.
Patrick R. Bartlow, Ph.D. Dissertation entitled "Design of *Escherichia coli* Host Strains for Improved Recombinant Protein Purification . . . ", Sep. 2011, University of Pittsburgh.
Le Cong et al. (2013) "Multiplex Genome Engineering Using CRISPR/Cas Systems", Science, vol. 339:819-823.
Jiang et al. (2013) "RNA-Guided Editing of Bacterial Genomes Using CRISPR/Cas Systems", Nature Biotechnology, vol. 31(3):233-239.
Mali et al. (2013) "Cas9 as a Versatile Tool for Engineering Biology", Nature Methods, vol. 10(10):957-963.
Sander et al. (2014) "CRISPR/Cas Systems for Editing, Regulating and Targeting Genomes", Nature Biotechnology, vol. 32(4):347-355.

Amrein et al. (1995) "Purification and characterization of recombinant human p50csk protein-tyrosine kinase from an *Escherichia coli* expression system overproducing the bacterial chaperones GroES and Gro EL", Proceedings of the National Academy of Sciences USA, vol. 92(4):1048-1052.
Shin et al. (2008) "Extracellular Recombinant Protein Production From an *Escherichia coli* lpp Deletion Mutant", Biotechnology and Bioengineering, vol. 101(6):1288-1296.
Posfai et al. (2006) "Emergent Properties of Reduced-Genome *Escherichia coli*", Science, vol. 312:1044-1046.
International Preliminary Report on Patentability dated Mar. 22, 2016 (including Written Opinion dated Dec. 8, 2014 (6 pages total)), and International Search Report dated Dec. 8, 2014, in priority PCT application PCT/US2014/056013.
Morimoto et al. (2008) "Enhanced Recombinant Protein Productivity by Genome Reduction in Bacillus subtilis", DNA Research, vol. 15:73-81.
Communication from the European Patent Office in counterpart European Patent Application EP13714069.5 dated Oct. 30, 2017 (8 pages total) and approved claims (4 pages total).
Notice of Intention to Grant from the European Patent Office in non-counterpart European Patent Application No. EP14846151.0 (21 pages total: 8 pages of Notice; 13 pages of claims), dated Jan. 26, 2018.

SEPARATOME-BASED PROTEIN EXPRESSION AND PURIFICATION PLATFORM

CROSS-REFERENCE TO RELATED APPLICATIONS

This application is a Continuation of and claims priority to U.S. application Ser. No. 14/521,845, filed Oct. 23, 2014, now U.S. Pat. No. 9,816,068, issued on Nov. 14, 2017; which is a Continuation of U.S. application Ser. No. 14/056,747, filed Oct. 17, 2013, now U.S. Pat. No. 8,927,231, issued Jan. 6, 2015; which is a Continuation of PCT application Serial No. PCT/US2013/030549, filed Mar. 12, 2013; which claims the benefit of priority of U.S. provisional application Ser. No. 61/610,298, filed Mar. 13, 2012. This application claims the benefit of priority of each of the listed prior applications, and the contents of each of these prior applications are herein incorporated by reference in their entirety.

STATEMENT REGARDING FEDERALLY SPONSORED RESEARCH OR DEVELOPMENT AND JOINT RESEARCH AGREEMENT DISQUALIFICATION UNDER THE CREATE ACT (COOPERATIVE RESEARCH AND TECHNOLOGY ENHANCEMENT ACT OF 2004 (CREATE ACT) (PUB. L. 108-453, 118 STAT. 3596 (2004))

This invention was made with government support under grants Nos. 0534836, 0533949, 1237252, 1142101, and 1048911, awarded by the National Science Foundation. The U.S. government has certain rights in the invention.

The present invention was collaboratively made by scientists from the University of Arkansas and the University of Pittsburgh under the above-noted joint NSF grants that were in effect on or before the date the presently claimed invention was made. The claimed invention was made as a result of activities undertaken within the scope of the joint research agreement. The term "joint research agreement" means the joint NSF research grants awarded to the above-noted parties for the performance of experimental, developmental, or research work in the field of the claimed invention.

BACKGROUND OF THE INVENTION

Field of the Invention

The present invention relates to a proteomics-based protein expression and purification platform, more particularly a single cell line, or set of cell lines, designed by manipulating the separatomes associated with various separation techniques, in particular column chromatography, that can be used in a wide variety of processes for the expression of recombinantly produced peptides, polypeptides, and proteins, and to the subsequent rapid, efficient, and economical recovery thereof in high yield, thereby eliminating the need to develop individualized host cells for each purification process.

Description of Related Art

Current society is heavily dependent on mass-manufactured peptides, polypeptides and proteins that are used in everything from cancer treatment medications to laundry detergents. More than 325 million people worldwide have been helped by the over 155 recombinantly produced polypeptides and peptides (drugs and vaccines) currently approved by the United States Food and Drug Administration. In addition, there are more than 370 biotechnology drug products and vaccines currently in clinical trials targeting more than 200 diseases, including various cancers, Alzheimer's disease, heart disease, diabetes, multiple sclerosis, immunodeficiency, and arthritis. Enzymes used in industrial processes claim approximately a $2.7 billion dollar market, with an expected growth to a value of $6 billion dollars by 2016. Of the approximately 3000 industrial enzymes in use today for applications in biotechnology, food, fuel, and pulp and paper industries, about one-third of these are produced in recombinant bacteria.

Manufacturing of therapeutically useful peptides, polypeptides, and proteins has been hampered, in large part, by the limitations of the organisms currently used to express these molecules, and of the often extensive recovery steps necessary as the final product is isolated. Recombinant protein expression is the preferred, predominant method for the manufacture of these pharmaceuticals, herein referred to as a "biologic" to differentiate them, in particular, both from chemically synthesized therapeutics (e.g., antihistamines or CNS drugs) and from industrial enzymes such as pectinases or restriction endonucleases, for example. In general, the purification of a biologic to within tolerable limits is the most costly stage of manufacturing and validation, with the burden of regulation placed upon it by the Food and Drug Administration (FDA) or similar (inter)national entity. Recombinant DNA techniques, hybridoma technologies, mammalian cell culturing, metabolic engineering, and fermentation improvements have permitted large-scale production of biologics.

As large-scale production issues are solved, manufacturing steps that limit productivity are shifted downstream. In an effort to quicken time-to-clinic and market, research efforts have focused on cutting material costs, improving productivity at large-scale, and developing robust, generic separation steps. In the biologics manufacturing process, cell lines are cultivated to produce, or express, the biologic; during this process, the desired biologic is expressed alongside unwanted host cell proteins. These contaminants then have to be separated from the biologic through expensive and time-consuming multi-step purification processes that often include centrifugation, ultrafiltration, extraction, precipitation, and the cornerstone of bioseparation, chromatographic separation. Since downstream processes account for 50% to 80% of total manufacturing costs, efforts to optimize purification of high-value, high-quality products are critical to success in the biopharmaceutical industry. For example, if there is a modest 5% loss of biologic per purification step, final yields of about 70% are encountered should the processing require 5-8 downstream steps. This overall loss is intolerable as market demands for biologics increase. End-uses for peptides, polypeptides, and proteins produced recombinantly, other than biologics, include, but are not limited to, diagnostic kits (e.g., glucose dehydrogenase for glucose sensing), enabling technologies (e.g., ligases for recombinant DNA efforts), consumer products (e.g., proteases for laundry soap), manufacturing (e.g., isomerases for production of corn syrup), and biofuel generation (e.g., cellulases for switchgrass processing). Materials of these product categories also suffer from the desire for efficient downstream processing, although their product validation is less stringent than for a biologic.

For the illustrations above, both recovery from the culture and purification are paramount. Challenges to the industry standard technique of column chromatography, a critical element to most bioseparation schemes, are dictated by lack of separation efficiency, the variety of chromatography separation media, and the diverse composition of the mobile phase. Lack of separation efficiency manifests itself predominantly as a reduction in column capacity, defined as the amount of target molecule bound per adsorption cycle, and selectivity, defined as the amount of target molecule bound divided by the total amount of material bound per adsorption cycle. The traditional method of addressing separation efficiency is empirical, and is driven by past experience because no software design tool, similar to CHEMCAD (chemical engineering) and SPICE (electrical engineering), for bioseparation process design exists in the public domain, if at all. Therefore, any improvements in the recovery of peptides, polypeptides, or proteins in terms of an increase in separation efficiency, column capacity in particular, have been traditionally gained by improvements in the properties of the chromatographic adsorbent, by artful design of the gradient used to elicit separation, or in some cases, by the enhancement of binding through the addition of $His_6$, maltose binding protein, $Arg_8$, or similarly designed affinity tails or tags. Although affinity tails or tags are widely used for purification of recombinant proteins, in particular through the use of $His_6$, the continued presence of genomic peptides, polypeptides, and proteins exhibiting affinity for the resins used in these chromatographic methods remains problematic. Notably, when host cell genomic peptides, polypeptides, and proteins are retained in the adsorption step, significant losses in column capacity and complications in gradient elution occur. Selection of companion chromatographic steps in a rational manner to increase separation efficiency, i.e., separation capacity (product recovery), separation selectivity (product purity), or both, is nearly impossible due to lack of knowledge regarding the contaminant species, and is therefore developed somewhat arbitrarily, requiring tedious, time-consuming, and expensive trial and error experimentation.

As disclosed herein, one route to supplement traditional means to aid in the purification of peptides, polypeptides, or proteins would be to alter the proteome of the host cell in order to reduce the burden of host cell contaminant adsorption. This concept is orthogonal to the series of patents and applications by Blattner et al. that disclose a number of different strains of *E. coli* engineered to contain reduced genomes—in contrast to the proteome—to facilitate the production of recombinant proteins (U.S. Pat. Nos. 8,178,339; 8,119,365; 8,043,842; 8,039,243; 7,303,906; 6,989,265; US20120219994A1; and EP1483367B1). U.S. Pat. No. 8,119,365 claims *E. coli* wherein the genome is between 4.41 Mb and 2.78 Mb. U.S. Pat. No. 8,043,842 claims *E. coli* wherein the genome is between 4.27 Mb and 4.00 Mb. U.S. Pat. No. 8,039,243 claims variously between 4.41 and 3.71 Mb, 4.31 Mb and 3.71 Mb, and 4.27 Mb and 3.71 Mb. U.S. Pat. No. 6,989,265 discloses *E. coli* wherein the genome is at least 5% to at least 14% smaller than the genome of its native parent strain. EP1483367B1 claims *E. coli* having a chromosome that is genetically engineered to be 5% to 40% smaller than the chromosome of its native parent *E. coli* strain.

These documents variously discuss the concepts of reduced genome *E. coli* for use in the production of recombinant proteins, improving recombinant protein expression in *E. coli* by improving the growth/yield properties and robustness as a recombinant host by eliminating large numbers of non-essential genes and improving *E. coli* transformation competence. Expression of endogenous/native proteins in host cells is also presumed to be reduced. None of these documents either discloses or discusses chromatographic purification procedures, or the optimization thereof in conjunction with the design of optimized host cells, to improve separation efficiency leading to a purified or partially purified target peptide, polypeptide, or protein.

U.S. 2009/0075352 discloses the use of in silico comparative metabolic and genetic engineering analyses to improve the production of useful substances in host strains by comparing the genomic information of a target strain for producing a useful substance to the genomic information of a strain that overproduces the useful substance by screening for, and by deleting genes unnecessary for the overproduction of the useful substance, thereby improving product yield. As in the case of the patent documents discussed above, this application does not disclose or discuss chromatographic purification procedures, or the optimization thereof to improve separation efficiency leading to a target peptide, polypeptide, or protein.

Yu et al. (2002) *Nature Biotechnol.* 20:1018-1023 discloses a method for determining essential genes in *E. coli* and minimizing the bacterial genome by deleting large genomic fragments, thereby deleting genes that are nonessential under a given set of growth conditions and identifying a minimized set of essential *E. coli* genes and DNA sequences. Neither the term "chromatography" nor "purification" is mentioned.

U.S. application 2012/0183995 discloses genetic modification of *Bacillus* species to improve the capacity to produce expressed proteins of interest, wherein one or more chromosomal genes are inactivated or deleted, or wherein one or more indigenous chromosomal regions are deleted from a corresponding wild-type *Bacillus* host chromosome. This includes removing large regions of chromosomal DNA in a *Bacillus* host strain wherein the deleted indigenous chromosomal region is not necessary for strain viability. These modifications enhance the ability of an altered *Bacillus* strain to express a higher level of a protein of interest over a corresponding non-altered *Bacillus* host strain. This application does not discuss improved chromatographic separation of expressed target recombinant peptides, polypeptides, or proteins from endogenous *Bacillus* proteins.

Asenjo et al. (2004), "Is there a rational method to purify proteins? From expert systems to proteomics", *Journal of Molecular Recognition* 17:236-247, discusses optimizing protein purification steps based on knowledge of the physicochemical properties of the target protein product and the protein contaminants. The paper notes "the rule of thumb that reflects the logic of first separating impurities present in higher concentrations." The concept of reduced genome host cells is not disclosed.

While the previously mentioned patents and journal articles do not disclose or discuss chromatographic purification procedures, other references either outline the general process by which data on host cell proteins that interact with chromatography media can be obtained, or focus on the elimination of product-specific impurities through gene knockout. Cai et al. (2004) *Biotechnol. Bioeng.* 88:77 and Tiwari et al. (2010) *Protein Expression and Purification* 70:191-195 disclose the application of cellular extracts of *E. coli* to various affinity and non-affinity chromatographic media, and the identification of adsorbed proteins by mass spectroscopy and 2D gel electrophoresis. While the metabolic characteristics of the proteins encountered were discussed, these references do not disclose any indications of improvement in separation efficiency. Liu et al. (2009) *J. Chromatog. A* 1216:2433-2438, Bartlow et al. (2011) *Protein Expression and Purification* 78:216-224, and Bartlow et al. (2012) *American Institute of Chemical Engineers Biotechnol. Prog.* 28:137-145 disclose the potential for improvement in product quality, purity in particular, should genes that express proteins that co-elute with histidine-extended Green Fluorescent Protein be deleted from the chromosome of *E. coli*. The quantitative data in this series of papers do not disclose or suggest improvements that lead to an increase in column capacity, nor do they demonstrate improvements that point to a universally applicable host strain with improved properties, useful for producing a variety of different peptides, polypeptides, or proteins, be they extended with an affinity tail or tag (or not). Indeed, should the genes identified and deemed important in Liu et al. (2009), supra, be deleted, an increase of significantly less than one percent (1%) in column capacity would be achieved. A similar argument for the deletion of genes responsible for product-specific contaminants applies to Caparon et al. (2010) *Biotechnol. Bioeng.* 105(2):239-249. This article discloses four specific gene deletions that improve the purity of the final biologic, since three of the proteins co-elute with the target and a fourth causes proteolytic degradation of the biologic. Lacking in this reference is a means of applying quantitative metrics to prioritize efforts that lead to increases in separation efficiency independent of target peptides, polypeptides, and proteins, and a method to interpret these data to prepare a host cell or set of host cells that provide increases in separation efficiency for as many different target molecules as possible.

In view of the foregoing, there exists a need for improved methods for recovering in quantity, and purifying, recombinant target peptides, polypeptides, and proteins from *E. coli* and other host cells routinely used for recombinant expression of, for example, therapeutic proteinaceous molecules and industrial enzymes. Development of bioseparation regimens can be challenging, requiring somewhat arbitrary trial and error combination of conventional chromatographic methods. The presence of host cell peptides, polypeptides, and proteins reduces separation step efficiency (adsorption and elution), and the tradeoff between overall yield and purity may not be optimal. Alternately, although the use of an affinity tail helps reduce the chromatographic space explored, it can still be plagued by co-adsorbing/co-eluting molecules, requiring further purification steps; addition/removal of the affinity tail via digestion steps; and cost (ligand and endonuclease).

The methods and host cells of the present invention address these problems and meet these needs. The present invention provides a novel route to supplement or supplant conventional methods to aid in the purification of target recombinant peptides, polypeptides, and proteins. This is accomplished by providing a rational scheme for altering the proteome of host cells used for expression in order to reduce the burden of adsorption of host cell peptides, polypeptides, and proteins that interfere with target molecule recovery and purification. This is accomplished by first identifying the separatome, defined as a sub-proteome associated with a separation technique, column chromatography for example, through a formal method that mathematically prioritizes specific modifications to the proteome via, for example, gene knockout, gene silencing, gene modification, or gene inhibition. Host cells, or sets of host cells, of the present invention display a reduced separatome, the properties of which lead to an increase in column capacity as peptides, polypeptides, or proteins with high affinity are eliminated first. Uniquely focusing on host cell peptides, polypeptides, or proteins with high affinity, rather than those with affinity similar to, or less than a presumed target recombinant molecule, facilitates a set of modifications that are useful for improving separation efficiency for a range of peptides, polypeptides, or proteins. Such high affinity host cell peptides, etc., are problematic regardless of the nature of the target recombinant molecule because not only can they display an elution profile that may decrease purity, but they also remain bound to the column due to the stringent conditions necessary for their desorption.

The separatome-based protein expression and purification platform disclosed herein provides the benefits of, but is not be limited to, reduction of the chromatography regimen, column capacity loss due to host cell contaminating peptide, polypeptide, and protein adsorption, and complexity of elution protocols since the number, and nature, of interfering peptides, polypeptides, and proteins to be resolved is less.

The present separatome-based protein expression and purification platform facilitates the modification of unoptimized host cell lines in order to eliminate the expression of undesirable, interfering peptides, polypeptides, and proteins during host cell cultivation, thereby reducing the total amount and cost of purification needed to produce a higher concentration, and absolute amount, of purified target recombinant product.

The separatome-based invention disclosed herein further provides a proteomics-based protein expression and purification platform based on a computer database and modeling system of separatome data for individually customized cell lines that facilitate recovery and purification of difficult to express, low yield proteins.

The separatome-based expression and purification platform disclosed herein also provides for modified host cell lines having a genome encoding and/or expressing a reduced number of nuisance or contaminating proteins, thereby decreasing the complexity and costs of the purification process.

Furthermore, the present invention provides a separatome-based expression and purification platform that utilizes an engineered series of broadly applicable bacterial and other host cells to provide facile purification systems for target recombinant peptide, polypeptide, and protein separation.

Compared to previous approaches involving the deletion of large numbers of host cell genes, the separatome-based method for designing host cells for expression of target peptides, polypeptides, and proteins provided herein is more "surgical", i.e., targeted and precise, and does not result in the deletion of large regions of host cell genomes. The present invention provides a rational framework for optimizing target recombinant peptide, polypeptide, or protein recovery and purification based on identification of host cell peptide, polypeptide, and protein contaminants that reduce the separation efficiency, i.e., separation capacity (product recovery), separation selectivity (product purity), or both, of target recombinant peptides, polypeptides, and proteins based on knowledge of the binding characteristics of contaminating species during chromatographic purification. This permits the coordinated design of universally useful, optimized host cells for target recombinant peptide, polypeptide, or protein expression and concomitant purification procedures using the smallest number of operations, and eliminates the need for arbitrary, tedious, time-consuming, and expensive trial and error experimentation. The methods disclosed herein avoid the need to design individualized host cell expression and chromatographic systems for specific recombinant target proteinaceous products, and provide a rational "separatomic" procedure and materials to eliminate and separate the main interfering peptide, polypeptide, and protein components of host cells using the minimum number of process steps. The present methods and host cells minimize, or in most cases, completely avoid the problems of eliminating host cell genes and proteins required for growth, viability, and target molecule expression that would adversely affect the use of such cells for expression of target recombinant peptides, polypeptides, and proteins. In some cases, the present engineered host cells exhibit improved growth, viability, and expression compared to the parental cells from which they are derived. This can be attributed, at least in part, to avoiding the problem of eliminating genes that are dispensable individually, but not in combination.

SUMMARY OF THE INVENTION

The present invention provides a separatome-based protein expression and purification platform comprising a system of separatome data for a host cell, which comprises data compiled on the genome and proteome sequences of the host cell, and a data visualization tool for graphically displaying such separatome data for identification and/or modification of contiguous or individual regions of nuisance or coeluting proteins of host cells. The separatome data can comprise data compiled on the metalloproteome and metabolome of the host cell. Host cells included in this platform include, for example, *Escherichia coli*, yeasts, *Bacillus subtilis* and other prokaryotes, and any of the other host cells conventionally used for expression of peptides, polypeptides, and proteins disclosed herein.

The system of separatome data is based on identified, conserved genomic regions of host cells that span resin- and gradient-specific chromatographies based on a relationship of binding properties of the peptides, polypeptides, and proteins encoded by the identified, conserved genomic regions for these chromatographies with the characteristics and location of genes on the chromosome(s) of host cells. The chromatographies include Immobilized-Metal Affinity Chromatography (IMAC), cation exchange chromatography (cation IEX), anion exchange chromatography (anion IEX), Hydrophobic Interaction Chromatography (HIC), or combinations thereof.

The present invention also encompasses a separatome-based protein expression and purification process for manufacturing of a modified cell line having a genome encoding a reduced number of contaminating peptides, polypeptides and proteins, wherein the process comprises the steps of:

(1) graphically displaying a separatome of a target host cell line as a visualization tool in conjunction with relevant biochemical information;

(2) identifying specific genes coding for contaminating peptides, polypeptides, and proteins for the target host cell line, and/or identifying specific genes encoding particular nuisance peptides, polypeptides, and proteins of the target host cell line;

(3) identifying, when possible, large contiguous genomic regions coding for contaminating peptides, polypeptides, and proteins for the target host cell line, and/or identifying specific genes encoding particular nuisance peptides, polypeptides, and proteins of the target host cell line;

(4) deleting the large contiguous genomic regions coding for contaminating peptides, polypeptides, and proteins, and/or the specific genes encoding particular nuisance peptides, polypeptides, and proteins, of the target host cell line from the genome of the target host cell by large scale or targeted knockout, respectively; and (5) deleting regions encoding any contaminant peptides, polypeptides, or proteins remaining in the genome of the target host cell after step (3) by gene specific knockout and/or PCR point mutation to form the modified cell line.

The target host cell can be selected from *Escherichia coli*, yeasts, *Bacillus subtilis* or other prokaryotes, or any of the other host cells conventionally used for expression disclosed herein.

In this process, the separatome is a system of chromatographic data of the juxtaposition of binding properties of peptides, polypeptides, and proteins encoded by identified, conserved genomic regions for chromatography methods with the characteristics and location of genes on the chromosome of the target host cell. The chromatographic methods of this process comprise Immobilized-Metal Affinity Chromatography (IMAC), cation exchange chromatography (cation IEX), anion exchange chromatography (anion IEX), Hydrophobic Interaction Chromatography (HIC), or combinations thereof.

In this process, step (1) further comprises identifying the contaminating proteins as essential and nonessential peptides, polypeptides, and proteins of the target host cell. Coding regions (genes) for essential peptides, polypeptides, and proteins can be reintroduced into the genome of the target host cell. The process can further comprise the step of constructing a larger fragment homologous to the target host cell. The fragment can be linear and sequenced with essential genes, and further comprises marker selection and selection removal.

The present invention also provides optimized strains of *Escherichia coli* modified by a separatome-based peptide, polypeptide, and protein expression and purification process, wherein the strain comprises a genome having (encoding) a reduced number of nuisance or coeluting peptides, polypeptides, and proteins. The separatome-based peptide, polypeptide, and protein expression and purification process can be a two-step purification process based on chromatotomes of combinations of chromatographies of *Escherichia coli*, and the nuisance or coeluting proteins can be reduced via large scale knockout, gene specific knockout, PCR point mutation, or a combination thereof.

More particularly, the present invention encompasses the following:

1. A host cell for expression of a target recombinant peptide, polypeptide, or protein, comprising:
   i) a reduced genome compared to the genome in the parent cell from which it is derived, or
   ii) a modified genome compared to the genome in the parent cell from which it is derived, or
   iii) in which expression of genes is reduced or completely inhibited compared to expression of said genes in the parent cell from which it is derived,
   wherein genes that are deleted, modified, or the expression of which is reduced or completely inhibited in said host cell, code for peptides, polypeptides, or proteins that impair the chromatographic separation efficiency of said target recombinant peptide, polypeptide, or protein expressed in said host cell.

2. The host cell of 1, wherein said chromatographic separation efficiency of said target recombinant peptide, polypeptide, or protein is improved compared to the chromatographic separation efficiency of said target recombinant peptide, polypeptide, or protein in the presence of peptides, polypeptides, or proteins coded for by said genes that are deleted, modified, or the expression of which is reduced or completely inhibited in said host cell upon affinity or adsorption, non-affinity column chromatography of said target recombinant peptide, polypeptide, or protein.

3. The host cell of 2, wherein improvement of said chromatographic separation efficiency of said target recombinant peptide, polypeptide, or protein is in the range of from about 5% to about 35%, or from about 10% to about 20%, compared to chromatographic separation efficiency of said target recombinant peptide, polypeptide, or protein in the presence of peptides, polypeptides, or proteins coded for by said genes that are deleted, modified, or the expression of which is reduced or completely inhibited in said host cell upon affinity or adsorption, non-affinity column chromatography of said target recombinant peptide, polypeptide, or protein.

4. The host cell of any one of 1-3, wherein said chromatographic separation efficiency is independent of elution conditions under which said target recombinant peptide, polypeptide, or protein emerges from an affinity or adsorption, non-affinity chromatography column as an enriched fraction.

5. The host cell of any one of 1-4, wherein deletion of said gene is performed by homologous recombination.

6. The host cell of any one of 1-4, wherein modification of said genes is performed by a method selected from the group consisting of point mutation, isozyme substitution, and transposon mutagenesis.

7. The host cell of any one of 1-4, wherein expression of said genes is reduced or completely inhibited by a method selected from the group consisting of RNA silencing, antisense oligonucleotide inhibition, and replacement of a native promoter with a weaker promoter.

8. The host cell of any one of 1-7, which exhibits about 75% to about 100% of the viability, growth rate, or capacity for expression of said target recombinant peptide, polypeptide, or protein expressed in said host cell compared to that of said parent cell from which it is derived, or which exhibits viability, growth rate, or capacity for expression of said target recombinant peptide, polypeptide, or protein expressed in said host cell greater than that of said parent cell from which it is derived.

9. The host cell of any one of 1-8, wherein said target recombinant peptide, polypeptide, or protein is present in a lysate of said host cell, or is secreted by said host cell.

10. The host cell of any one of 1-9, wherein said target recombinant peptide, polypeptide, or protein is an endogenous peptide, polypeptide, or protein.

11. The host cell of 10, wherein said endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

12. The host cell of any one of 1-9, wherein said target recombinant peptide, polypeptide, or protein is a heterologous peptide, polypeptide, or protein.

13. The host cell of 12, wherein said heterologous peptide, polypeptide, or protein is selected from the group consisting of an enzyme and a therapeutic peptide, polypeptide, or protein.

14. The host cell of 13, wherein said enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and said therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, tissue plasminogen activator, and insulin.

15. The host cell of any one of 1-14, which is selected from the group consisting of a bacterium, a fungus, a mammalian cell, an insect cell, a plant cell, and a protozoal cell.

16. The host cell of 15, wherein said bacterium is *E. coli, B. subtilis, P. fluorescens*, or *C. glutamicum*; said fungus is a yeast selected from the group consisting of *S. cerevisiae* and *K. pastoris*; said mammalian cell is a CHO cell or a HEK cell; said insect cell is an *S. frugiperda* cell; said plant cell is a tobacco, alfalfa, rice, tomato, or soybean cell; and said protozoal cell is a *L. tarentolae* cell.

17. The host cell of 16, wherein said bacterium is *E. coli*.

18. The *E. coli* host cell of 17, wherein said parent cell from which said *E. coli* host cell is derived is selected from the group consisting of *E. coli* K-12, *E. coli* MG, *E. coli* BL, and *E. coli* DH.

19. The host cell of 16, wherein said bacterium is *B. subtilis*.

20. The *B. subtilis* host cell of 19, wherein said parent cell from which said *B. subtilis* host cell is derived is selected from the group consisting of *B. subtilis* 168 and *B. subtilis* BSn5.

21. The host cell of 16, wherein said *S. cerevisiae* and *K. pastoris* are selected from the group consisting of *S. cerevisiae* S288c and AWRI796, and *K. pastoris* CBS7435 and GS115, respectively.

22. The host cell of 16, wherein said CHO cell is CHO-K1 and said HEK cell is HEK 293.

23. The *E. coli* parent cell of 18, which is selected from the group consisting of *E. coli* K-12, *E. coli* MG1655, *E. coli* BL21 (DE3), and *E. coli* DH10B.

24. *E. coli* strain K-12, MG1655, BL21 (DE3), and DH10B of 23, having a genome comprising the nucleotide sequence disclosed in the reference of Table Entry Number 1, 2, 3, and 4, respectively, in Table 1.

25. *B. subtilis* strain 168 and BSn5 of 20, having a genome comprising the nucleotide sequence disclosed in the reference of Table Entry Number 1 and 2, respectively, in Table 2.

26. *S. cerevisiae* strain S288c and AWRI796 of 21, having a genome comprising the nucleotide sequence disclosed in the reference of Table Entry Number 1 and 2, respectively, in Table 3.

27. *K. pastoris* strain CBS7435 and GS115 of 21, having a genome comprising the nucleotide sequence disclosed in the reference of Table Entry Number 1 and 2, respectively, in Table 4.

28. CHO cell strain CHO-K1 of 22, having a genome comprising the nucleotide sequence disclosed in the reference of Table Entry Number 1 in Table 5.

29. HEK cell strain HEK 293 of 22, having a genome comprising the nucleotide sequence disclosed in the reference of Table Entry Number 1 in Table 6.

30. The *E. coli* host cell of any one of 16-18 or 23-24, wherein said reduced genome compared to the genome in the parent cell from which it is derived is less than 5% smaller, less than about 4.5% smaller, less than about 4% smaller, less than about 3.5% smaller, less than about 3% smaller, less than about 2.5% smaller, less than about 2% smaller, less than about 1.5% smaller, or less than about 1% smaller, than the genome of said parent cell from which it is derived.

31. The *E. coli* host cell of any one of 16-18 or 23-24, wherein said reduced genome compared to the genome in the parent cell from which it is derived is between about 4.17 Mb to about 4.346 Mb.

32. An *E. coli* host cell for expression of a target recombinant peptide, polypeptide, or protein, comprising:

i) a reduced genome compared to the genome in the parent cell from which it is derived, or ii) a modified genome compared to the genome in the parent cell from which it is derived, or iii) in which expression of genes is reduced or completely inhibited compared to expression of said genes in the parent cell from which it is derived, wherein said parent cell is *E. coli* strain K-12, MG1655, BL21 (DE3), or DH10B, having a genome comprising the nucleotide sequence disclosed in the reference of Table Entry Number 1, 2, 3, and 4, respectively, in Table 1, and wherein genes that are deleted, modified, or the expression of which is reduced or completely inhibited in said host cell compared to expression of said genes in said parent cell from which it is derived, code for proteins that impair the chromatographic separation efficiency of said target recombinant peptide, polypeptide, or protein expressed in said host cell in the presence of peptides, polypeptides, or proteins coded for by said genes that are deleted, modified, or the expression of which is reduced or completely inhibited in said host cell, and that elute from a chromatographic affinity column having a ligand, in a buffer comprising a compound that dictates adsorption to its respective ligand during equilibration and elution from said affinity column, in an amount in the range, in a combination selected from the group consisting of the combinations in the following table A:

wherein said parent cell is *E. coli* strain K-12, MG1655, BL21 (DE3), or DH10B, having a genome comprising the nucleotide sequence disclosed in the reference of Table Entry Number 1, 2, 3, and 4, respectively, in Table 1, wherein genes that are deleted, modified, or the expression of which is reduced or completely inhibited in said host cell, code for host cell peptides, polypeptides, or proteins that impair the chromatographic separation efficiency of said target recombinant peptide, polypeptide, or protein expressed in said host cell, and wherein genes that are deleted, modified, or the expression of which is reduced or completely inhibited in said host cell compared to expression of said genes in said parent cell from which it is derived, code for proteins that impair the chromatographic separation efficiency of said target recombinant peptide, polypeptide, or protein expressed in said host cell in the presence of peptides, polypeptides, or proteins coded for by said genes that are deleted, modified, or the expression of which is reduced or completely inhibited in said host cell, and that elute from a chromatographic adsorption, non-affinity column having a ligand, in a buffer comprising a compound that dictates adsorption to its respective ligand during equilibration and elution from said adsorption, non-affinity column, in an amount in the range, in a combination selected from the group consisting of the combinations in the following table B:

TABLE A

| Ligand | Compound in Buffer That Dictates Adsorption to Affinity Column During Equilibration and Causes Elution From Column | Concentration or pH Range |
|---|---|---|
| Glutathione S-transferase | Glutathione | from about 0 mM to about 10 mM |
| Amino acid (e.g., lysine) | A common salt | from about 0 mM to about 2M |
| Amino acid | pH | from about pH 2 to about pH 11 |
| Avidin | A chaotropic salt | from about 0M to about 4M |
| Avidin | pH | from about pH 2 to about pH 10.5 |
| Carbohydrate (e.g., Dextrin) | Sugar or isocratic (e.g., maltose) | from about 0 mM to about 10 mM |
| Carbohydrate | pH | from about pH 5 to about pH 8 |
| Organic dye (e.g., Cibacron Blue) | A common salt | from about 0 mM to about 1.5M |
| Organic dye | pH | from about pH 4 to about pH 8 |
| Organic dye | Imidazole or a common salt | from about 5 mM to about 250 mM |
| Divalent metal (e.g., Ni(II)) | pH | from about pH 4 to about pH 12 |
| Divalent metal (e.g., Ni(II)) | Imidazole | from about 5 mM to about 500 mM |
| Heparin | A common salt | from about 0 mM to about 2M |
| Protein A or Protein G | Glycine | from about 0 mM to about 100 mM |
| Protein A or Protein G | pH | from about pH 3 to about pH 7 |
| IgG | Glycine | from about 0 mM to about 100 mM |
| Coenzyme | Competing Protein | from about 1 mM to about 12 mM |

33. An *E. coli* host cell for expression of a target recombinant peptide, polypeptide, or protein, comprising:

i) a reduced genome compared to the genome in the parent cell from which it is derived, or ii) a modified genome compared to the genome in the parent cell from which it is derived, or iii) in which expression of genes is reduced or completely inhibited compared to expression of said genes in the parent cell from which it is derived,

TABLE B

| Ligand | Compound in Buffer That Dictates Adsorption to Non-Affinity Column During Equilibration and Causes Elution From Column | Concentration or pH Range |
|---|---|---|
| Ion exchange | Common salt | from about 0M to about 2M |

TABLE B-continued

| Ligand | Compound in Buffer That Dictates Adsorption to Non-Affinity Column During Equilibration and Causes Elution From Column | Concentration or pH Range |
| --- | --- | --- |
| Ion exchange | pH | from about pH 2 to about pH 12 |
| Reverse phase | Organic solvent ex. Acetonitrile | from about 0% to about 100% |
| Hydrophobic interaction | Common salt | from about 2M to about 0M |

34. The *E. coli* host cell of 32 or 33, wherein said common salt is selected from the group consisting of a chloride salt, a sulfate salt, an acetate salt, a carbonate salt, and a propionate salt.

35. The *E. coli* host cell of 33, wherein said organic solvent is selected from the group consisting of acetonitrile, methanol, and 2-propanol.

36. The *E. coli* host cell of 33, wherein genes that are deleted, modified, or the expression of which is inhibited, in the genome of said *E. coli* host cell are selected from the group consisting of the genes listed in Table C:

TABLE C

| GeneName |
| --- |
| rpoC |
| rpoB |
| hldD |
| metH |
| entF |
| mukB |
| tgt |
| rnr |
| glgP |
| recC |
| ycaO |
| glnA |
| ptsI |
| metE |
| sucA |
| hrpA |
| groL |
| gatZ |
| speA |
| thiI |
| nusA |
| tufA |
| degP |
| clpB |
| rapA |
| metL |
| ycfD |
| nagD |
| ilvA |
| fusA |
| cyaA |
| gldA |
| dnaK |
| ygiC |
| gyrA |
| glnE |
| carB |
| ppsA |
| degQ |
| usg |
| ilvB |
| thrS |
| recB |
| entB |
| dusA |
| typA |

TABLE C-continued

| GeneName |
| --- |
| prs |
| cysN |
| atpD |
| purL | and combinations thereof.

37. The *E. coli* host cell of 33, wherein said parent cell *E. coli* strain is MG1655 (genotype: Wild Type: F-, λ_-, rph-1), and the following combinations of genes are deleted, modified, or the expression of which is inhibited: LTS00 (genotype: ΔthyA); LTS01+ (genotype: ΔmetH); LTS01 (genotype: ΔthyAΔmetH); LTS02+ (genotype: ΔmetHΔentF); LTS02 (genotype: ΔthyAΔmetHΔentF); LTS03+ (genotype: ΔmetHΔentFΔtgt); LTS03 (genotype: ΔthyAΔmetHΔentFΔtgt); LTS04+ (genotype: ΔmetHΔentFΔtgtΔrnr); LTS04 (genotype: ΔthyAΔmetHΔentFΔtgtΔrnr); or LTS05+ (genotype: ΔmetHΔentFΔtgtΔrnrΔycaO).

38. The host cell of any one of 1-37, wherein increased separation efficiency is manifested as increased separation capacity, increased separation selectivity, or both.

39. The host cell of 38, wherein separation capacity is defined as the amount of target recombinant peptide, polypeptide, or protein adsorbed to said column per mass lysate in the case where said target recombinant peptide, polypeptide, or protein is not secreted, or mass culture medium in the case where said target recombinant peptide, polypeptide, or protein is secreted, applied to said column, and separation selectivity is defined as the amount of target recombinant peptide, polypeptide, or protein adsorbed to said column per total peptide, polypeptide, or protein adsorbed to said column.

40. The host cell of 38 or 39, wherein said increased separation capacity is in the range of from about 5% to about 35%.

41. The host cell of any one of 1-40, wherein separation of said target recombinant peptide, polypeptide, or protein from host cell peptides, polypeptides, or proteins is performed by column chromatography employing a solid phase chromatography medium.

42. The host cell of 41, wherein said column chromatography is selected from the group consisting of affinity chromatography employing an affinity ligand bound to said solid phase, and adsorption-based, non-affinity chromatography.

43. The host cell of 42, wherein said affinity ligand is selected from the group consisting of an amino acid, a divalent metal ion, a carbohydrate, an organic dye, a coenzyme; glutathione S-transferase, avidin, heparin, protein A, and protein G.

44. The host cell of 43, wherein said divalent metal ion is selected from the group consisting of $Cu^{++}$, $Ni^{++}$, $Co^{++}$, and $Zn^{++}$; said carbohydrate is selected from the group consisting of maltose, arabinose, and glucose; said organic dye is a dye comprising a triazene moiety; and said coenzyme is selected from the group consisting of NADH and ATP.

45. The host cell of 42, wherein said adsorption-based, non-affinity chromatography is selected from the group consisting of ion exchange chromatography, reverse phase chromatography, and hydrophobic interaction chromatography.

46. The host cell of 45, wherein said adsorption-based, non-affinity chromatography is ion exchange chromatography.

47. The host cell of 46, wherein said ion exchange chromatography employs a ligand selected from the group consisting of diethylaminoethyl cellulose (DEAE), monoQ, and S.

48. The host cell of any one of 41 to 47, wherein said host cell peptides, polypeptides, or proteins that impair separation efficiency of said target recombinant peptide, polypeptide, or protein expressed in said host cell are peptides, polypeptides, or proteins that are strongly retained during column chromatography.

49. The host cell of 48, wherein said host cell peptides, polypeptides, or proteins that are strongly retained during ion exchange chromatography are those that are retained during elution with a mobile phase comprising a common salt in the range of from about 5 mM to about 2,000 mM.

50. The host cell of 49, wherein said host cell peptides, polypeptides, or proteins that are strongly retained during ion exchange chromatography are those that are retained during elution with a mobile phase comprising a common salt in the range of from about 500 mM to about 1,000 mM.

51. The host cell of any one of 41 to 50, wherein said host cell peptides, polypeptides, or proteins that impair the separation efficiency of said target recombinant peptide, polypeptide, or protein expressed in said host cell are peptides, polypeptides, or proteins that are weakly retained during column chromatography.

52. The host cell of 50, wherein said host cell peptides, polypeptides, or proteins that are weakly retained during chromatography are those that are retained during elution with a mobile phase comprising a common salt in the range of from about 5 mM to about 500 mM.

53. The host cell of 52, wherein said host cell peptides, polypeptides, or proteins that are weakly retained during chromatography are those that are retained during elution with a mobile phase comprising a common salt in the range of from about 10 mM to about 350 mM.

54. The host cell of any one of 41 to 53, wherein said host cell peptides, polypeptides, or proteins that impair the separation efficiency of said target recombinant peptide, polypeptide, or protein expressed in said host cell are peptides, polypeptides, or proteins that are both strongly retained and weakly retained during column chromatography.

55. A separatome of chromatographically relevant host cell peptides, polypeptides, and proteins for column affinity chromatography employing an affinity ligand bound to a solid phase or column adsorption-based, non-affinity chromatography, comprising host cell peptides, polypeptides, and proteins based on their capacity recovery potential from said column,
wherein said capacity recovery potential of said host cell peptides, polypeptides, and proteins is quantitatively determined by:
(a) scoring a peptide, polypeptide, or protein (i) with the formulae:

$$importance_i = \sum_j \left[ b_1 \left( \frac{y_{cj}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i$$

with values for a series of peptides, polypeptides, and proteins written in descending order (largest value close to unity downwards to the smallest value), followed by
(b) calculating the capacity recovery potential of a relevant peptide, polypeptide, or protein (i) given by:

$$recovery\ potential_i = h_{i,total}/h_{total,ms}.$$

wherein the following definitions apply: $y_{cj}$ and $y_{max}$=concentration of mobile phase eluent in fraction (j) and maximum value, respectively; and $h_{i,j}$ and $h_{i,total}$=the amount of protein (i) in fraction (j) and total bound protein (i), respectively; $h_{j,total}$=total amount of protein in fraction (j); $h_{total,ms}$=total mass of protein bound to column; $b_1$=scaling parameter; $\alpha$=steric factor; $MW_i$ and $MW_{ref}$=molecular weight of protein (i) or reference protein, respectively.

56. The separatome of 55, wherein said affinity ligand in said column affinity chromatography employing an affinity ligand bound to a solid phase is selected from the group consisting of an amino acid, a divalent metal ion, a carbohydrate, an organic dye, a coenzyme, glutathione S-transferase, avidin, heparin, protein A, and protein G.

57. The separatome of 56, wherein peptides, polypeptides, and proteins are eluted from said affinity chromatography column using an elution agent y selected from the group consisting of a common salt, hydronium ion, imidazole, glutathione, a chaotropic salt, heparin, and glycine.

58. The separatome of 55, wherein said column adsorption-based, non-affinity chromatography is selected from the group consisting of ion exchange chromatography, reverse phase chromatography, and hydrophobic interaction chromatography.

59. The separatome of 58, wherein peptides, polypeptides, and proteins are eluted from said adsorption-based, non-affinity chromatography column using an elution agent y selected from the group consisting of a common salt, hydronium ion, and an organic solvent.

60. The separatome of 57 or 59, wherein said common salt is selected from the group consisting of a chloride salt, a sulfate salt, an acetate salt, a carbonate salt, and a propionate salt.

61. The separatome of 59, wherein said organic solvent is selected from the group consisting of methanol, 2-propanol, and acetonitrile.

62. The separatome of 57, wherein said chaotropic salt is guanidine hydrochloride.

63. The separatome of any one of 55-62, wherein the maximum value of said elution agent y is defined by $y_{max}$ in 55.

64. The separatome of any one of 55-63, which is in a form selected from the group consisting of a table, a visual representation such as a figure, and a computer file.

65. The separatome of chromatographically relevant host cell peptides, polypeptides, or proteins for column affinity chromatography employing an affinity ligand bound to a solid phase of any one of 55-57, 60, or 62-64.

66. The separatome of chromatographically relevant host cell peptides, polypeptides, or proteins for column adsorption-based, non-affinity chromatography of any one of 55, 58-61, or 63-64.

67. A method for designing a reduced or modified proteome host cell, or a host cell in which expression of genes is reduced or completely inhibited compared to expression of said genes in the parent cell from which said host cell is derived, for expression of a target recombinant peptide, polypeptide, or protein to improve the chromatographic separation efficiency of said target recombinant peptide, polypeptide, or protein expressed in said host cell, comprising identifying and ranking proteins of chromatographic relevance that adversely affect said separation efficiency of said target recombinant peptide, polypeptide, or protein in a parent cell from which said host cell is derived by:
i) equilibrating an affinity chromatography column employing an affinity ligand bound to a solid phase, or an adsorption-based, non-affinity chromatography column, using a mobile loading or eluting phase, or an operational variable;
ii) in the case where said target recombinant peptide, polypeptide, or protein is not secreted, fractionating a lysate of said host cell, or in the case where said target recombinant peptide, polypeptide, or protein is secreted from said host cell, fractionating the culture medium in which said host cell is grown, on said column by applying an elution gradient to elute peptide, polypeptide, or protein fractions from said column;
iii) identifying, quantifying, and scoring peptides, polypeptides, or proteins in said fractions eluted from said column;
iv) assessing the metabolic role of said peptides, polypeptides, or proteins identified in step iii) that affect column capacity; and
v) designing a reduced or modified genome host cell, or a host cell in which expression of genes is reduced or completely inhibited compared to expression of said genes in the parent cell from which said host cell is derived, to modify the proteome of said parent cell from which said host cell is derived in order to increase chromatographic separation efficiency based on steps iii) and iv).

68. The method of 67, further comprising reducing or modifying the genome of said parent cell from which said host cell is derived, or reducing or completely inhibiting the expression of peptides, polypeptides, or proteins in said parent cell, to increase chromatographic separation efficiency based on step v), thereby producing a host cell comprising a reduced or modified genome compared to the genome in said parent cell from which said host cell is derived, or a host cell in which expression of peptides, polypeptides, or proteins is reduced or completely inhibited.

69. The method of 67 or 68, wherein said reduced or modified proteome host cell, or said host cell host cell in which expression of (n) genes is reduced or completely inhibited compared to expression of said genes in the parent cell from which said host cell is derived, facilitates an overall capacity recovery of said target recombinant peptide, polypeptide, or protein in the range of from about 5%, from about 10%, from about 20%, from about 30%, from about 40%, from about 50%, from about 60%, from about 70%, from about 80%, from about 90%, or from about 95%, to about 100%, wherein capacity recovery is defined by summing (n) values of recovery potential for individual (i) proteins by the following:

$$\text{capacity recovery} = 100\% \times \sum_{i=1}^{n} \text{recovery potential}_i$$

wherein n=total number of proteins that are deleted, inhibited, or modified, and i=an individual protein.

A preferred range for capacity recovery is from about 3% to about 50%, more preferably from about 5% to about 40%, or from about 5% to about 35%, 70. The method of any one of 67-69, wherein step i) is modified by varying the characteristics of said mobile loading or eluting phase or operational variable.

71. The method of any one of 67-70, wherein identification of said peptides, polypeptides, or proteins in step iii) is performed by comparing the LC-MS signature of said peptides, polypeptides, or proteins to publicly available standards.

72. The method of any one of 67-71, wherein quantification of said proteins in step iii) is performed using spectral counting, or a combination of Bradford protein assay, 2-dimensional electrophoresis, and densitometry.

73. The method of any one of 67-72, wherein said scoring in step iii) is calculated as in 55.

74. The method of any one of 67-73, wherein assessing the metabolic role of identified proteins in step iv) is performed by bioinformatics techniques.

75. A method of enriching the amount of a target recombinant peptide, polypeptide, or protein relative to other peptides, polypeptides, or proteins present in an initial protein mixture comprising said target recombinant peptide, polypeptide, or protein, comprising:
i) selecting a chromatography medium that binds said target recombinant peptide, polypeptide, or protein from the group consisting of an affinity chromatography medium and an adsorption-based, non-affinity chromatography medium;
ii) in the case where an affinity chromatography medium is selected, expressing said target recombinant peptide, polypeptide, or protein in said host cell of any one of 1-32, 34, 36, 38-44, 48, or 51-54;
iii) in the case where an adsorption-based, non-affinity chromatography medium is selected, expressing said target recombinant peptide, polypeptide, or protein in said host cell of any one of 1-31, 33-35, 37-42, or 45-54; and
iv) chromatographing said initial protein mixture comprising said target recombinant peptide, polypeptide, or protein using said chromatography medium of step ii) or step iii), as appropriate, and collecting elution fractions, thereby obtaining one or more fractions containing an enriched amount of said target recombinant peptide, polypeptide, or protein relative to other peptides, polypeptides, or proteins in said fraction compared to the amount of said target recombinant peptide, polypeptide, or protein relative to other peptides, polypeptides, or proteins in said initial protein mixture.

76. The method of 75, further comprising chromatographing an enriched fraction of step iv) to obtain said target recombinant peptide, polypeptide, or protein in a desired degree of purity.

77. The method of 76, further comprising recovering said target recombinant peptide, polypeptide, or protein.

78. A method of preparing a pharmaceutical or veterinary composition comprising a recombinant therapeutic peptide, polypeptide, or protein, comprising:
i) selecting a chromatography medium that binds said recombinant therapeutic peptide, polypeptide, or protein from the group consisting of an affinity chromatography medium and an adsorption-based, non-affinity chromatography medium;
ii) in the case where an affinity chromatography medium is selected, expressing said recombinant therapeutic peptide, polypeptide, or protein in said host cell of any one of 1-32, 34, 36, 38-44, 48, or 51-54;
iii) in the case where an adsorption-based, non-affinity chromatography medium is selected, expressing said recombinant therapeutic peptide, polypeptide, or protein in said host cell of any one of 1-31, 33-35, 37-42, or 45-54;
iv) in the case where said recombinant therapeutic peptide, polypeptide, or protein is not secreted from said host cell, preparing a lysate of said host cell containing said recombinant therapeutic peptide, polypeptide, or protein, producing an initial recombinant therapeutic peptide-, polypeptide-, or protein-containing mixture; or v) in the case where said recombinant therapeutic peptide, polypeptide, or protein is secreted from said host cell, harvesting culture medium in which said host cell is grown, containing said recombinant therapeutic peptide, polypeptide, or protein, thereby obtaining an initial recombinant therapeutic peptide-, polypeptide-, or protein-containing mixture;

vi) chromatographing said initial recombinant therapeutic peptide-, polypeptide-, or protein-containing mixture of step iv) or step v) using said chromatography medium of step i) or step ii), as appropriate, and collecting elution fractions, thereby obtaining one or more fractions containing an enriched amount of said recombinant therapeutic peptide, polypeptide, or protein relative to other peptides, polypeptides, or proteins in said fraction compared to the amount of said recombinant therapeutic peptide, polypeptide, or protein relative to other peptides, polypeptides, or proteins in said initial protein mixture;

vii) further chromatographing an enriched fraction of step vi) to obtain said recombinant peptide, polypeptide, or protein in a desired degree of purity;

viii) recovering said recombinant therapeutic peptide, polypeptide, or protein; and ix) formulating said recombinant therapeutic peptide, polypeptide, or protein with a pharmaceutically or veterinarily acceptable carrier, diluent, or excipient to produce a pharmaceutical or veterinary composition, respectively.

79. A method of purifying a recombinant enzyme, comprising:
   i) selecting a chromatography medium that binds said recombinant enzyme from the group consisting of an affinity chromatography medium and an adsorption-based, non-affinity chromatography medium;
   ii) in the case where an affinity chromatography medium is selected, expressing said recombinant enzyme in said host cell of any one of 1-32, 34, 36, 38-44, 48, or 51-54;
   iii) in the case where an adsorption-based, non-affinity chromatography medium is selected, expressing said recombinant enzyme in said host cell of any one of 1-31, 33-35, 37-42, or 45-54;
   iv) in the case where said recombinant enzyme is not secreted from said host cell, preparing a lysate of said host cell containing said recombinant enzyme, producing an initial recombinant enzyme-containing mixture; or
   v) in the case where said recombinant enzyme is secreted from said host cell, harvesting culture medium in which said host cell is grown, containing said recombinant enzyme, thereby obtaining an initial recombinant enzyme-containing mixture;
   vi) chromatographing said initial recombinant enzyme-containing mixture of step iv) or step v) using said chromatographic medium of step i) or step ii), as appropriate, and collecting elution fractions, thereby obtaining one or more fractions containing an enriched amount of said recombinant enzyme relative to other peptides, polypeptides, or proteins in said fraction compared to the amount of said recombinant enzyme relative to other peptides, polypeptides, or proteins in said initial protein mixture;
   vii) further chromatographing an enriched fraction of step vi) to obtain said recombinant enzyme in a desired degree of purity; and
   viii) recovering purified recombinant enzyme.

80. The method of 79, further comprising placing said purified recombinant enzyme in a buffer solution in which said purified recombinant enzyme is stable and retains enzymatic activity.

81. The method of 80, wherein said purified recombinant enzyme-containing buffer solution is reduced to dryness.

82. The method of 81, wherein said dry purified recombinant enzyme-containing buffer solution is in the form of a powder.

83. A kit, comprising said host cell of any one of 1-54 or 68-69.

84. The kit of 83, further comprising instructions for expressing a target recombinant peptide, polypeptide, or protein in said host cell.

85. The kit of 84, wherein said target recombinant peptide, polypeptide, or protein is an endogenous or heterologous target recombinant peptide, polypeptide, or protein.

86. The kit of any one of 83-85, wherein said instructions further comprise directions for purifying said expressed target recombinant peptide, polypeptide, or protein by affinity chromatography or adsorption-based, non-affinity chromatography.

87. The kit of any one of 83-86, further comprising a chromatographic resin for affinity chromatography or adsorption-based, non-affinity chromatography.

88. A method of enriching a target peptide, polypeptide, or protein from a mixture obtained from a host cell, comprising:
   a. chromatographing said mixture via affinity chromatography or adsorption-based, non-affinity chromatography;
   b. collecting an elution fraction that contains an enriched amount of said target peptide, polypeptide, or protein in said fraction compared to the amount of said peptide, polypeptide, or protein of interest in said mixture; and
   c. recovering said target peptide, polypeptide, or protein from said elution fraction, wherein said host cell is derived from a parent cell, and has:
      i) a reduced genome compared to the genome in the parent cell from which it is derived, or
      ii) a modified genome compared to the genome in the parent cell from which it is derived, or
      iii) in which expression of genes is reduced or completely inhibited compared to expression of said genes in the parent cell from which it is derived,
      wherein genes that are deleted, modified, or the expression of which is reduced or completely inhibited in said host cell, code for peptides, polypeptides, or proteins that impair the chromatographic separation efficiency of said target peptide, polypeptide, or protein expressed in said host cell in said affinity chromatography or said adsorption-based, non-affinity chromatography.

89. The method of 88, wherein said mixture is a lysate of said host cell in the case where said peptide, polypeptide, or protein accumulates intracellularly, or is medium in which said host cell is grown in the case where said peptide, polypeptide, or protein is secreted by said host cell.

90. The method of 88 or 89, further comprising chromatographing said target peptide, polypeptide, or protein of step c. in order to obtain said target peptide, polypeptide, or protein in a desired degree of purity.

91. The method of 90, further comprising recovering purified target peptide, polypeptide, or protein.

The methods of 88-91 encompass the use of all of the parent cells, host cells, and methods, etc., disclosed herein, and described in 1-87, above.

Further scope of the applicability of the present invention will become apparent from the detailed description and drawing(s) provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed descriptions taken in conjunction with the accompanying drawing(s), all of which are given by way of illustration only, and are not limitative of the present invention, in which:

FIG. 1 relates to the detailed description of the invention. FIGS. 2, 5, and 6 relate to Example 2, Construction of the Ion Exchange Separatome of *E. coli* and Its Use to Design and Build Novel Host Strains for a Common Chromatography Resin. FIGS. 3 and 4 refer to Example 1, Identification of Host Cell Proteins Associated With a Specific Product, Histidine-Tagged Green Fluorescent Protein, as a Comparative Example.

DETAILED DESCRIPTION OF THE INVENTION

Figure 1:
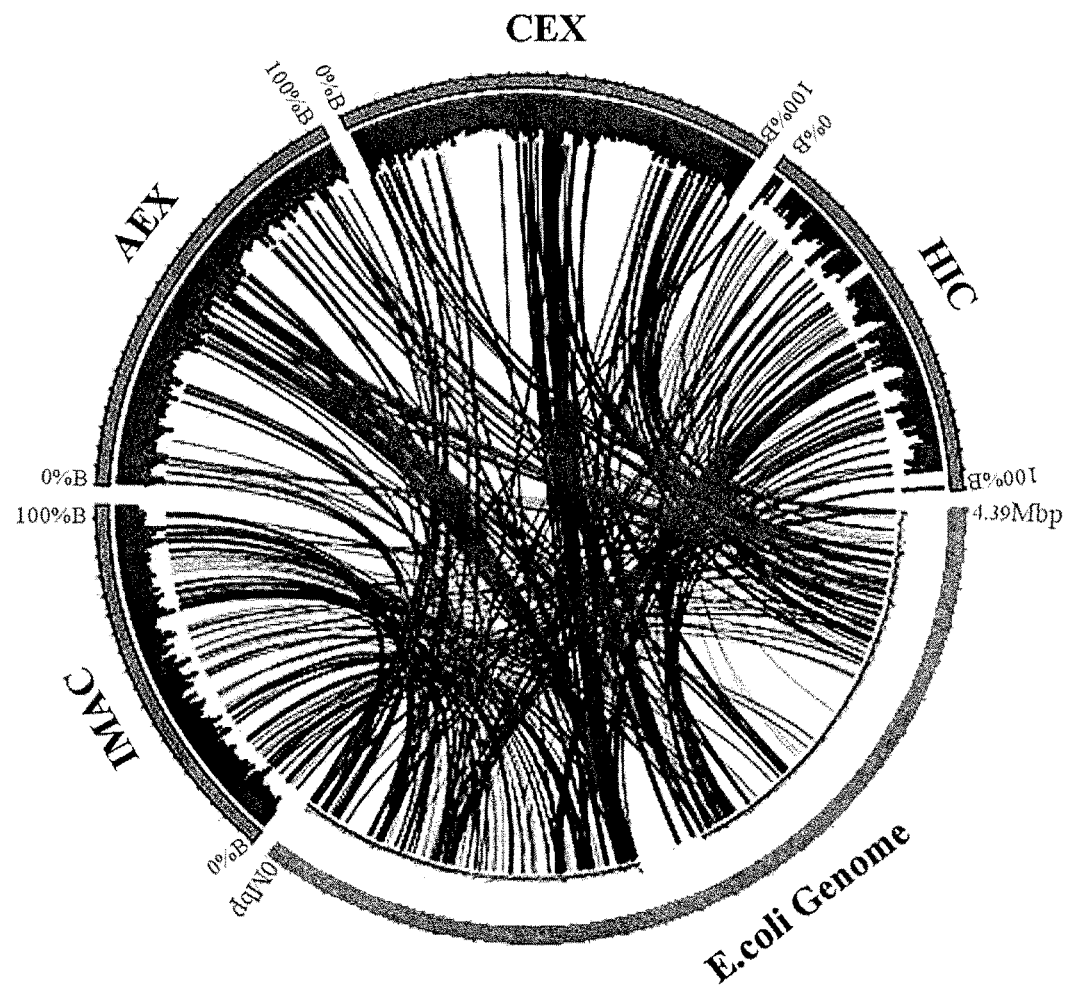
FIG. 1 shows a CIRCOS® rendering of model data used to describe multiple separatomes. CIRCOS® is a software package that applies the circular ideogram layout to display relationships between genomic intervals. It is described in Krzywinski et al. (2009) "Circos: an Information Aesthetic for Comparative Genomics", *Genome Res.* 19:1639-1645. In the figure, the ring is comprised of segments that represent either gene positions or % B. Four different separatomes associated with popular methods of chromatography (IMAC, immobilized metal affinity chromatography; AEX, anion exchange chromatography; CEX, cation exchange chromatography; and HIC, hydrophobic interaction chromatography) are represented. Connecting lines map individual proteins contained within a separatome to their gene (located on the outer ring), with the concentric (inner gray) ring describing the concentration of the protein found in the fractions as they elute from a column as indicated by the length of the black bar segments. Other data that could be depicted in a CIRCOS® rendering include gene designation, essentiality of gene product, metabolic category, or other parameter, placed on a series of concentric rings or attached to the connecting lines, for example as shown by the other concentric ring fragment.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein is herein incorporated by reference in its entirety.

As noted above, Asenjo et al. (2004), "Is there a rational method to purify proteins? From expert systems to proteomics", *Journal of Molecular Recognition* 17:236-247, points out that, "Until now, it has been virtually impossible to select separation and purification operations for proteins either for therapeutic or analytical application in a rational manner due to lack of fundamental knowledge on the molecular properties of the materials to be separated and the lack of an efficient system to organize such information." The present invention provides solutions to this problem.

The inventions disclosed herein include a separatome-based protein expression and purification platform based on the juxtaposition of the chromatographic binding properties of genomic peptides, polypeptides, and proteins with the characteristic and location of genes on the target chromosome, such as those of *E. coli, Bacillus subtilis*, yeasts, and other host cells. The separatome-based protein expression and purification platform maps the separatome of target chromosomes based on relationships between the loci of genes associated with nuisance peptides, polypeptides, and proteins. In addition, the separatome-based protein expression and purification platform reduces the genome of host cells through precisely targeted modifications to create custom, robust target host strains with reduced nuisance peptides, polypeptides, and proteins. Moreover, the present separatome-based protein expression and purification platform provides a computerized knowledge tool that, given separatome data regarding a target peptide, polypeptide, or protein, intuitively suggests strategies leading to efficient purification. The separatome-based protein expression and purification platform is an efficient bioseparation system that intertwines host cell strain and chromatography.

Definitions

The following definitions are provided to aid the reader in understanding the various aspects of the present invention. Unless defined otherwise, all technical and scientific terms used herein have the same meaning as commonly understood by those of ordinary skill in the art to which the invention pertains.

"An affinity ligand" for affinity chromatography refers to a chemical moiety, coupled to a stationary phase, that serves as a biospecific sorptive group.

"Host cell" refers to a cell used to express an endogenous or heterologous nucleic acid sequence encoding a target peptide, polypeptide, or protein of interest.

"Parent cell from which it is derived" refers to a cell that is modified to serve as a host cell of the present invention. As a non-limiting example, an *E. coli* parent cell can be a conventional *E. coli* K-12 cell.

The phrase "a target recombinant therapeutic peptide, polypeptide, or protein" and the like refers to a peptide, polypeptide, or protein exhibiting human or veterinary medicinal properties, expressed using recombinant nucleic acid methodology. As used herein, "medicinal properties" broadly includes not only medical therapeutic applications, but use for nutritional purposes and personal care as well.

The phrase "endogenous target recombinant peptide, polypeptide or protein" and the like refers to a peptide, polypeptide, or protein native to a host cell, which is expressed in such cell using recombinant nucleic acid methodology.

It should be noted that the present invention, including all the parent cells, host cells, methods, etc., disclosed herein, are applicable not only to the expression and purification of endogenous peptides, polypeptides, or proteins via recombinant methods, but also to the expression and purification of endogenous peptides, polypeptides, and proteins that are naturally expressed within host cells, i.e., without the application of recombinant methodology.

The phrase "heterologous target recombinant peptide, polypeptide or protein" and the like refers to a peptide, polypeptide, or protein not native to a host cell, which is expressed in such cell using recombinant nucleic acid methodology.

The phrase "a modified genome compared to the genome in the parent cell from which it is derived" refers to modification of genes to abate the undesirable effect(s) of the gene products on separation efficiency performed by, for example, point mutation, isozyme substitution, transposon mutagenesis, etc. As indicated, modification includes gene substitution.

"Proteome" refers to a collection of identifiable proteins expressed by a host cell.

"Chromatotome" refers to a proteome defined by a set of host cell proteins that bind a chromatographic stationary phase.

"Separatome" refers to a proteome defined by a set of host cell proteins that are associated with a separation technique (not limited to packed bed chromatography).

"Metalloproteome" refers to a proteome with the identifying characteristic of interaction with metals or metal ions.

"Metabolome" refers to a collection of small-molecule metabolites like glucose-6-phosphate and other molecules of similar molecular weight.

"Separation efficiency" is manifested as separation capacity, separation selectivity, or both. In many cases, separation capacity is a more important parameter for the practice of the present invention.

"Separation capacity" refers to the amount of peptides, polypeptides, and/or proteins that can be captured during the loading cycle of a chromatographic separation. Separation capacity is defined as the amount of target recombinant peptide, polypeptide, or protein adsorbed by a column per mass lysate fed to the column. The present invention encompasses increases in separation capacity in the range of from about 5% to about 35% or more. Such increases reflect an advantage of the present separatome invention concept over the separation capacities achievable using standard extraction and purification methods.

"Separation selectivity" refers to the amount of target protein/total protein captured by a chromatographic adsorbent. Separation selectivity is defined as the amount of target recombinant peptide, polypeptide, or protein adsorbed by the column per total protein adsorbed to the column.

"Percent B" refers to a proportion or amount, expressed as a number between 0 and 100%, of a mixture fed to a chromatography column comprised of a blend of two fluids of different compositions, i.e., composition A and composition B. As % B increases, the change in mobile phase composition causes proteins to be eluted in a differential fashion, beginning with those of low affinity.

"Strongly retained" refers to peptides, polypeptides, and proteins that elute from a chromatography column upon desorption due to stringent changes in mobile phase composition identified by "percent B".

"Weakly retained" refers to peptides, polypeptides, and proteins that elute from a chromatography column upon desorption due to small changes in mobile phase composition identified by "percent B".

"Common salt" refers to a compound that dissociates in water to form a cation and an anion, such as a chloride salt, a sulfate salt, an acetate salt, a carbonate salt, a propionate salt, etc., as would be apparent to one of ordinary skill in the art. Common cations in such salts are, for example, sodium, potassium, and ammonium cations.

The phrase "chromatographically relevant host cell peptides, polypeptides, or proteins for column affinity chromatography or column adsorption-based, non-affinity chromatography" refers to proteins of a separatome or chromatotome.

"Importance" refers to the degree to which, should a host cell peptide, polypeptide, or protein be deleted, modified, or inhibited, capacity recovery is impacted. Proteins of chromatographic relevance are considered important should large gains in capacity recovery be achieved through deletion, modification, or inhibition. "Important" proteins are therefore a subset of relevant proteins.

"Reduced" in the context of the level of expression of peptides, polypeptides, or proteins from host cell genes refers to diminution in the amount of such expression products in the range of from about 5% to about 95%, more preferably from about 10% to about 95%, or more, compared to the level of such products normally observed in parent cells from which such host cells are derived.

"Scoring" refers to rank ordering members of a separatome to identify host cell peptides, polypeptides, or proteins that impair the chromatographic separation efficiency of a target recombinant peptide, polypeptide, or protein expressed in the host cell, and to establish quantitative improvements gained through their elimination.

"Operational variable" refers to a condition or operating parameter that leads to different Damkohler, Biot, or Peclet numbers used to describe a separation technique.

"Purify, purifying, purified" and the like refer to the process by which a peptide, polypeptide, or protein in a mixture is enriched so as to contain lesser amounts of materials derived from the host cell in which it is expressed, and the enriched product, respectively.

"Plant cells" includes cells of flowering and non-flowering plants, as well as algal cells, for example *Chlamydomonas, Chlorella*, etc.

Certain claims have unique formulae to mathematically define the non-metabolic aspects of the separatome, with specific regard to the overall impact a peptide, polypeptide, or protein has on column efficiency. A peptide, polypeptide, or protein elutes or emerges from a column as a peak of material, first at low concentration increasing to a maximum value, then decreasing back to zero, in the characteristic shape of a bell-like curve. The peak adopts a shape that may be described as sharp/narrow, with the majority of material of interest contained in a few fractions; broad/shallow, with the majority of material present in multiple fractions; or something in between. The time (retention time) at which the peak emerges is governed by binding strength. Peptides, polypeptides, and proteins with high affinity towards a ligand require more stringent conditions for desorption to occur, whereas those with low affinity pass through the column unretained. The ability to capture both phenomena, namely peak shape and retention time, is important to quantitatively establish the chromatographic relevance of a peptide, polypeptide, or protein. Once the relevance for a set of peptides, polypeptides, or proteins is established, molecular biology techniques are then used to delete, modify, inhibit the expression of, or substitute genes associated with these interfering molecules to directly increase column capacity and indirectly enhance purity.

Defining "recovery potential" for protein (i) first involves determining the fractional capacity occupied by this particular host cell protein by:

$$\text{recovery potential}_i = h_{i,total}/h_{total,ms}$$

with $h_{total,ms}$=total amount of host cell proteins bound to column, and $h_{i,total}$=the bound amount attributed to (i). The value of recovery potential is bound by zero and one, with a value of one indicative of a single host cell protein, if removed from the separatome, would achieve complete recovery of the column capacity. Extending this argument to the removal of (n) proteins, the term "capacity recovery" is defined in general as:

$$\text{capacity recovery} = 100\% \times \sum_{i=1}^{n} \text{recovery potential}_i$$

where the sigma operator allows one to sum the individual contributions for the set of (n) proteins. In the equation, n refers to number of proteins, and i is an individual protein.

These two simple relationships provide the starting point to define how much capacity can be gained as genes are deleted, modified, inhibited, or substituted. The relationships do not, however, establish order or priority within the context of peak shape and retention time. The latter is important to the disclosed invention because as mentioned previously, it is desired to focus efforts on common, problematic host cell proteins rather than those that are specific to a target recombinant product. Strongly retained or high affinity host cell proteins that are bound and that subsequently reduce column capacity would be generally problematic due to their persistent presence. Other qualifiers generally regarded as problematic would include high molecular weight (steric effects at high loading), sensitivity to proteolysis (multiple peaks or broad peak for a single protein), and propensity for subunit adsorption (multiple peaks or broad peak for a single protein). A criterion has been developed to score the "importance" of a protein (i) within a separatome, namely:

$$\text{importance}_i = \sum_j \left[ b_1 \left( \frac{y_{c_j}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i$$

with the following definitions: $b_1$=scaling parameter; $y_{c_j}$ and $y_{max}$=concentration of mobile phase eluent in fraction (j) and maximum value, respectively; $h_{i,j}$ and $h_{i,total}$=the amount of protein (i) in fraction (j) and total bound protein (i), respectively; $h_{j,total}$=total amount of protein in fraction (j); $MW_i$=molecular weight of protein (i); $MW_{ref}$=molecular weight of a reference protein within the separatome; $\alpha$=steric factor; and i=protein. These ratio terms—the y's and h's-adopt values between 0 and 1, yet hold different significances. A protein that remains bound and requires stringent conditions for elution reflects a y ratio to be close to, if not equal to, unity. A protein that emerges as a tight peak presents with a ratio for h close to unity, and finally, should that emerging peak constitute the majority of fraction (j), the third ratio would be close to unity. Multiplying each ratio, and summing the product of these ratios for each fraction (j) where (i) is present provides a quantitative ranking. For example, a protein that is retained at high NaCl concentration and emerges as a sharp peak would be deemed chromatographically relevant and will be scored as high with this formula. A second example would be a protein that broadly elutes. It would also receive a high score or relevancy because its score would be high by virtue of its presence in multiple fractions.

Lastly, there requires a consideration of steric effects. As a chromatography column becomes loaded, larger proteins interact with multiple ligands either directly through adsorption, or indirectly through hindrance of binding. When steric effects require consideration, the basic equation contains a molecular weight ratio raised to a power that is descriptive of these phenomena. A non-zero alpha in the above equation, with a preferred value between 0 and 1, would indicate some degree of steric effects. Note that the general form of the importance equation also permits scale-parameters ($b_1$) to adjust the weighting of a particular score. For example, $b_1$ may be used to indicate metabolic necessity ($b_1=0$), meaning a zero value will force a low score because it likely will not be deleted form the genome.

To summarize, the basic form of the equation favors the elimination or deletion of peptides, polypeptides, or proteins that have high affinity toward the adsorbent, with some degree of freedom to permit the tailoring of the modifications should the host cell be expressly used for a single recombinant DNA product and not a variety of products.

Commercially Important Protein Products

Exemplary, non-limiting, commercially important peptide, polypeptide, and protein products that can be expressed, recovered, and purified using the host cells, methods, and separatome information disclosed herein include, but are not limited to, the following.

Therapeutic Proteins

Examples of therapeutic human proteins that have been synthesized from genes cloned in bacteria and/or eukaryotic cells, or by expression in plants or animals, include antibodies and antigen-binding fragments; vaccines; $\alpha_1$-Antitrypsin (emphysema); deoxyribonuclease (cystic fibrosis); epidermal growth factor (ulcers); erythropoietin (anemia); Factor VIII (hemophilia); Factor IX (Christmas disease); fibroblast growth factor (ulcers); follicle stimulating hormone (infertility treatment); granulocyte colony stimulating factor (cancers); insulin (diabetes); insulin-like growth factor 1 (growth disorders); interferon-$\alpha$ (leukemia and other cancers); interferon-$\beta$ (cancers, AIDS); interferon-$\gamma$ (cancers, rheumatoid arthritis); interleukins (cancers, immune disorders); lung surfactant protein (respiratory distress); relaxin (aid in childbirth); serum albumin (plasma supplement); somatostatin (growth disorders); somatotrophin (growth disorders); superoxide dismutase (free radical damage in kidney transplants); tissue plasminogen activator (heart attack); tumor necrosis factor (cancers).

Proteins and Enzymes Used in Analytical Applications

In addition to the use of antibodies and enzymes as therapeutic agents, they are also used in the diagnosis of diseases as the components of some confirmatory tests of certain diagnostic procedures. Hexokinase and glucose oxidase are used in the quantification of glucose in the serum and urine. Glucose-oxidase is used in glucose electrodes. Uricase is used for the estimation of uric acid present in urine. Alkaline phosphatase, horseradish peroxidase, and antibodies are used in ELISA (Enzyme Linked Immunosorbent Assay).

Industrial Enzymes and Proteins

Industrially useful enzymes include carbohydrate-hydrolyzing enzymes such as amylases, cellulase, invertases, etc.; proteolytic enzymes such as papain, trypsin, chymotrypsin, etc.; and other bacterial and fungal-derived proteolytic enzymes and lipases that can hydrolyze various types of lipids and fats. All these enzymes are important in the food and beverage industries, the textile industry, paper industry, and detergent industry. Proteases have a special use in the beverage industry, meat and leather industries, cheese production, detergent industry, bread, and confectionary industry. Various types of lipases are used for the modifications of various types of lipids and fats, production of various organic acids including fatty acids, in detergents, and production of cocoa butter. In addition to all these, enzymes are used in chemical industries as reagents in organic synthesis for carrying out stereospecific reactions.

Non-catalytic Functional Proteins

These commercially important proteins are used in the food industry as emulsifiers, for inducing gelation, water binding, foaming, whipping, etc. These non-catalytic functional proteins are classified as whey proteins. The proteins that remain in solution after the removal of casein are by definition called whey proteins.

Commercially available whey protein concentrates contain 35% to 95% protein. If they are added to food on a solid's basis, there will be large differences in functionality due to the differences in protein content. Most food formulations call for a certain protein content and thus whey-protein concentrates are generally utilized as a constant protein base. In this case, the differences due to protein content as such should be eliminated. As the protein content increases, the composition of other components in the whey-protein concentrate must also change and these changes in composition have an effect on functionality.

Nutraceutical Proteins

Nutraceutical proteins represent a class of nutritionally-important proteins having therapeutic activity. The whey-protein concentrates and some of the milk proteins of infant foods contain certain pharmaceutical proteins having high nutritive quality. Infants get the required proteins from the mother's milk, which also contains certain therapeutic proteins that protect the baby from infection and other problems. There are other infant foods, which also have more or less the same composition as that of mother's milk, made up of cow's and buffalo's milk. All these food proteins provide the infants the raw building materials in the form of essential amino acids and at the same time protect them from microbial infections and other diseases.

Large scale Enzyme applications

Detergents

Bacterial proteinases are still the most important detergent enzymes. Lipases decompose fats into more water-soluble compounds. Amylases are used in detergents to remove starch based stains.

Starch Hydrolysis and Fructose Production

The use of starch degrading enzymes was the first large scale application of microbial enzymes in food industry. Mainly two enzymes carry out conversion of starch to glucose: alpha-amylase and fungal enzymes. Fructose is produced from sucrose as a starting material. Sucrose is split by invertase into glucose and fructose, and fructose is separated and crystallized.

Beverages

Enzymes have many applications in the beverage industry. Lactase splits milk-sugar lactose into glucose and galactose. This process is used for milk products that are consumed by lactose intolerant consumers. Addition of pectinase, xylanase, and cellulase improve the liberation of the juice from pulp. Similarly, enzymes are widely used in wine production.

Textiles

The use of enzymes in the textile industry is one of the most rapidly growing fields in industrial enzymology. The enzymes used in the textile field are amylases, catalase, and lactases, which are used to remove starch, degrade excess hydrogen peroxide, bleach textiles, and degrade lignin Animal Feed Addition of xylanase to wheat-based broiler feed has increased the available metabolizable energy 7-10% in various studies. Enzyme addition reduces viscosity, which increases absorption of nutrients, liberates nutrients either by hydrolysis of non-degradable fibers or by liberating nutrients blocked by these fibers, and reduces the amount of feces.

Baking

Alpha-amylases have been most widely studied in connection with improved bread quality and increased shelf life. Use of xylanases decreases the water absorption, and thus reduces the amount of added water needed, in baking. This leads to more stable dough. Proteinases can be added to improve dough-handling properties; glucose oxidase has been used to replace chemical oxidants and lipases to strengthen gluten, which leads to more stable dough and better bread quality.

Pulp and Paper

The major application in the pulp and paper industry is the use of xylanases in pulp bleaching. This considerably reduces the need for chlorine based bleaching chemicals. In paper making, amylase enzymes are used especially in modification of starch. Pitch is a sticky substance present mainly in softwoods. Pitch causes problems in paper machines and can be removed by lipases.

Leather

The leather industry uses proteolytic and lipolytic enzymes in leather processing. Enzymes are used to remove unwanted parts. In dehairing and dewooling phases, bacterial proteases are used to assist the alkaline chemical process. This results in a more environmentally friendly process and improves the quality of the leather. Bacterial and fungal enzymes are used to make leather soft and easier to dye.

Specialty Enzymes

There are a large number of specialty applications for enzymes. These include the use of enzymes in analytical applications, flavor production, protein modification, personal care products, DNA-technology, and in fine chemical production.

Enzymes in Analytics

Enzymes are widely used in clinical analytical methodology. Contrary to bulk industrial enzymes, these enzymes need to be free from side activities. This means that elaborate purification processes are needed.

An important development in analytical chemistry is biosensors. The most widely used application is a glucose biosensor involving glucose oxidase catalyzed reaction. Several commercial instruments are available which apply this principle for measurement of molecules like glucose, lactate, lactose, sucrose, ethanol, methanol, cholesterol, and some amino acids.

Enzymes in Personal Care Products

Personal care products are a relatively new area for enzymes. Proteinase and lipase containing enzyme solutions are used for contact lens cleaning. Hydrogen peroxide is used in disinfections of contact lenses. The residual hydrogen peroxide after disinfections can be removed by catalase. Some toothpaste contains glucoamylase and glucose oxidase. Enzymes are also being studied for applications in skin and hair care products.

Enzymes Used in DNA-Technology

DNA-technology is an important tool in the enzyme industry. Most traditional enzymes are produced by organisms that have been genetically modified to overproduce desired enzymes. Recombinant DNA methodology has been used to engineer overproducing microorganisms, and employs enzymes such as nucleases (especially restriction endonucleases), ligases, polymerases, and DNA-modifying enzymes to modify genes and construct necessary expression cassettes and vectors.

Enzymes in Fine Chemical Production

In spite of some successes, commercial production of chemicals by living cells via pathway engineering is still in many cases the best alternative to apply biocatalysis. Isolated enzymes have, however, been successfully used in fine chemical synthesis. Some of the most important examples are:

Chirally Pure Amino Acids and Aspartame

Natural amino acids are usually produced by microbial fermentation. Novel enzymatic resolution methods have been developed for the production of L- and D-amino acids. Aspartame, the intensive non-calorie sweetener, is synthesized in non-aqueous conditions by thermolysin, a proteolytic enzyme.

Rare Sugars

Recently, enzymatic methods have been developed to manufacture practically all D- and L-forms of simple sugars. Glucose isomerase is one of the important industrial enzymes used in fructose manufacturing.

Semisynthetic Penicillins

Penicillin is produced by genetically modified strains of *Penicillium* strains. Most of the penicillin is converted by immobilized acylases to 6-aminopenicillanic acid, which serves as a backbone for many semisynthetic penicillins.

Lipase-Based Reactions

In addition to detergent applications, lipases can be used in versatile chemical reactions since they are active in organic solvents. Lipases are used in transesterification, for enantiomeric separation of alcohols, and for the separation of racemic mixtures. Lipases have also been used to form aromatic and aliphatic polymers.

Enzymatic Oligosaccharide Synthesis

The chemical synthesis of oligosaccharides is a complicated multi-step effort. Biocatalytic syntheses with isolated enzymes like glycosyltransferases and glycosidases or engineered whole cells are powerful alternatives to chemical methods. Oligosaccharides have found applications in cosmetics, medicines and as functional foods.

Overview of the Invention

The present invention provides a separatome-based host cell peptide, polypeptide, and protein expression and purification platform focusing on the proteomes of various chromatographic methods to provide a single host cell line, or set of host cell lines, that can be used for expression of a wide variety of recombinant peptides, polypeptides, and proteins, thereby eliminating the need to develop individual host cell lines for each purification process.

The "separatome" of the present separatome-based protein expression and purification platform involves the juxtaposition of the binding properties of host cell peptides, polypeptides, and proteins in common chromatographic techniques (e.g., IMAC, IEX, and/or HIC) with the characteristics and location of the corresponding encoding genes on the target host cell chromosome(s). While the examples of the separatome-based protein expression and purification platform disclosed herein focus on *Escherichia coli* as the host cell, and its chromatotome, the invention is not limited thereto as the separatome-based peptide, polypeptide, and protein expression and purification platform can extend to any suitable host conventionally used for recombinant expression, such as *Lactococcus lactis*, *Bacillus* species such as *B. licheniformis*, *B. amyloliquefaciens*, and *B. subtilis*, *Corynebacterium glutamicum*, *Pseudomonas fluorescens*, or other prokaryotes; fungi, including various yeasts such as *Saccharomyces cerevisiae*, *Pichia* (now K) *pastoris*, and *Pichia methanolica*; insect cells; mammalian cells; plant cells, including for example, tobacco (e.g., cultivars BY-2 and NT-1), alfalfa, rice, tomato, soybean, as well as algal cells; and protozoal cells such as the non-pathogenic strain of *Leishmania tarentolae*, etc.

The present separatome-based peptide, polypeptide, and protein expression and purification platform is an efficient bioseparation system that intertwines host cell strain and chromatography. Since the high cost of product purification often limits the availability of therapeutic proteins of interest to immunology, vaccine development, pharmaceutical production, and diagnostic reagents, as well as the availability of enzymes for various applications, the present separatome-based peptide, polypeptide, and protein expression and purification platform provides alternative pathways towards efficient purification based on the utilization of proteome data. In particular, the separatome-based protein expression and purification platform provides for: (i) a system of chromatographic data based on identified, conserved genomic regions that span resin- and gradient-specific chromatographies, or chromatotomes, for example, a database of *E. coli* proteins that span the chromatography total contaminant pool (TCP)/elution contaminant pool (ECP) and bind under various conditions to a variety of chromatographic resins; (ii) a process to minimize contaminant pools of nuisance or coeluting proteins associated with specific chromatographies, for example, gradients that substantially decrease the number of coeluting proteins encountered during bioseparation, and the specific, targeted deletion of nuisance host cell peptide-, polypeptide-, and protein-encoding genes to minimize contaminant pools associated with affinity adsorption and non-affinity adsorption chromatographies, including IMAC, cation IEX, anion IEX, HIC, and combinations thereof.

The separatome-based peptide, polypeptide, and protein expression and purification platform is constructed based upon a computer system of identified, conserved genomic regions that span resin- and gradient specific-chromatographies, or chromatotomes. The computer system includes a data visualization program/application resident on a standard computer device, such as a mainframe, desktop, or other computer. For example, the computer may have a central processor that controls the overall operation of the computer and a system bus that connects the central processor to one or more conventional components, such as a network card or modem. The computer may also include a variety of interface ports and drives for reading and writing data or files. A user of the separatome-based protein expression and purification platform can interact with the computer with a keyboard, pointing device, microphone, pen device, or other input device. The computer may be connected via a suitable network connection, such as a T1 line, a common local area network ("LAN"), via the worldwide web, or via other mechanism for connecting computer devices.

Figure 2:
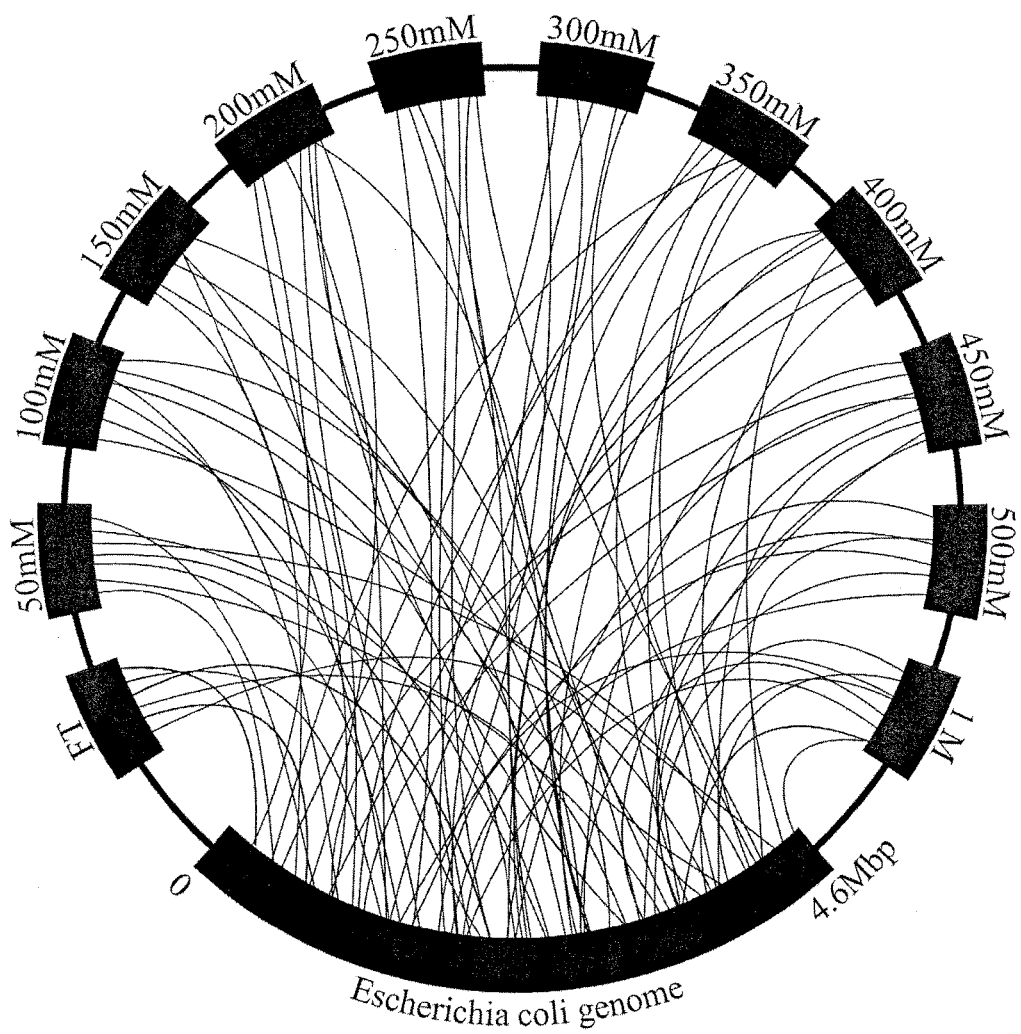
FIG. 2 shows a CIRCOS® rendering of model data describing the separatome of *E. coli* for ion exchange chromatography. Similar to FIG. 1 is the use of connecting lines that indicate genes associated with proteins found in the separatome of *E. coli* for a particular resin/equilibrating condition. However, this rendering provides detail as to the elution fraction by connecting a gene to a particular box on the ring that represents a salt concentration. The lower black fragment of the circle entitled "*Escherichia coli* genome" can contain the location of genes present on the *E. coli* chromosome. Each box represents a different cut from a column.

The separatome-based peptide, polypeptide, and protein expression and purification platform will utilize large amounts of data compiled on the metalloproteome and metabolome of the selected host cell, such as *E. coli*. The data visualization program/application, such as CIRCOS®, a software package for visualizing data and information in a circular layout (available from Canada's Michael Smith Genome Sciences Center), enables the user to visualize the large amounts of data and information for exploring relationships between objects or positions. FIGS. 1 and 2 illustrates examples of how the data visualization program/application could illustrate the *E. coli* chromosome mapped with the chromatotome of multiple chromatographic techniques, thus showing where the different chromatotomes lie within the greater genome. Each line in FIG. 1 represents a single contaminating protein, and the graph at its base shows the total concentration of the protein as a percent of the TCP or ECP. If each TCP is subdivided into its respective ECPs, then further corollaries can be drawn between proteins and genomic location. Further, segments of the ring represent the *E. coli* genome or the proteome associated with a particular isolation technique. With respect to *E. coli*, inner rings can represent additional information like essentiality, successful deletion, metabolic function, etc. For a given chromatographic technique, inner ring data can represent conditions that trigger adsorption or elution, concentration in the extract, and if this protein is differentially expressed during stress.

In addition, the separatome-based peptide, polypeptide, and protein expression and purification platform may utilize and/or incorporate data about the target genome and proteome sequences, such as from ECOGENE® (Institute for Advanced Biosciences, Keio University and Integrated Genomics, Chicago, Ill.), a database and website that reports the structural and functional annotation of *Escherichia coli* K-12 described in Zhou et al. (2013) *Nucleic Acids Research* 41, Database issue, (D1): D613-D624. doi: 10.1093/nar/gks1235. The data visualization program/application of the separatome-based protein expression and purification platform provides the user a feasible means of utilizing the data by melding it into a productive format, and in particular, the data visualization program/application provides the ability to visually summarize large collections of data covering peptides, polypeptides, and proteins encountered in the chromatotome and their essentiality.

The mapping and plotting of the IMAC, IEX and HIC data by the separatome-based peptide, polypeptide, and protein expression and purification platform allows for the identification of large contiguous regions of contaminants from several chromatography techniques that may be targeted for modification if necessary.

Since the overall structure of a target recombinant peptide, polypeptide, or protein and the column resin are usually fixed constraints, a reduction in contaminant species has the ability to improve chromatographic recovery and purification via elimination of undesirable binding events. Overall reduction of contaminant species, including undesired host cell peptides, polypeptides, and proteins, can be achieved by removal, modification, or inhibition of the expression of the genomic regions coding for the contaminants.

General Methods

Practice of the present invention employs, unless otherwise indicated, conventional techniques of molecular biology, recombinant DNA technology, microbiology, chemistry, etc., which are well known in the art and within the capabilities of those of ordinary skill in the art. Such techniques include the following non-limiting examples: preparation of cellular, plasmid, and bacteriophage DNA; manipulation of purified DNA using nucleases, ligases, polymerases, and DNA-modifying enzymes; introduction of DNA into living cells; cloning vectors for various organisms; PCR; gene deletion, modification, replacement, or inhibition; production of recombinant peptides, polypeptides, and proteins in host cells; chromatographic methods; etc.

Such methods are well known in the art and are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; Amberg et al. (2005) *Methods in Yeast Genetics: A Cold Spring Harbor Laboratory Course Manual*, 2005 Edition, Cold Spring Harbor Laboratory Press; Roe et al. (1996) *DNA Isolation and Sequencing: Essential Techniques*, John Wiley & Sons; J. M. Polak and James O'D. McGee (1990) *In Situ Hybridization: Principles and Practice*; Oxford University Press; M. J. Gait (Editor) (1984) *Oligonucleotide Synthesis: A Practical Approach*, IRL Press; D. M. J. Lilley and J. E. Dahlberg (1992) *Methods in Enzymology: DNA Structure Part A: Synthesis and Physical Analysis of DNA*, Academic Press; and *Lab Ref A Handbook of Recipes, Reagents, and Other Reference Tools for Use at the Bench*, Edited by Jane Roskams and Linda Rodgers (2002) Cold Spring Harbor Laboratory Press; Burgess and Deutscher (2009) *Guide to Protein Purification*, Second Edition (*Methods in Enzymology*, Vol. 463), Academic Press. Note also U.S. Pat. Nos. 8,178,339; 8,119,365; 8,043,842; 8,039,243; 7,303,906; 6,989,265; US20120219994A1; and EP1483367B1. The entire contents of each of these texts and patent documents is herein incorporated by reference.

Methods for Deleting, Modifying, and Inhibiting the Expression of Genes

Baba et al. (2006) *Mol. Syst. Biol.* 2:2006.0008 discloses methods for making precisely defined single gene deletions in *E. coli*.

Datsenko et al. (2000) *Proc. Natl. Acad. Sci. USA*. 97(12): 6640-5 discloses methods for inactivating chromosomal genes in *E. coli* using PCR products.

Stringer et al. (2012) *PLoS ONE* 7(9): e44841. doi: 10.1371/journal.pone.0044841 discloses a rapid, efficient, PCR-based recombineering method that can be used to introduce scar-free point mutations, deletions, epitope tags, and promoters into the genomes of multiple species of enteric bacteria.

Methods for RNA silencing and antisense oligonucleotide inhibition of gene expression are well known in the art. Note, for example, the reviews in *Nature* (2009) 457, No. 7228, pp. 395-433 and *Molecular Cancer Therapeutics* (2002) 1:347-355, respectively.

Frequently Used Expression Systems for Foreign Genes

Yin et al. (2007) *Journal of Biotechnology* 127(3):335-347 reviews the most frequently used expression systems for foreign genes.

Listed below are a number of representative papers describing protein production in frequently used host cell systems.

Expression in *E. coli*

Baneyx (1999) *Curr. Opin. Biotechnol.* 10(5): 411-21.

Expression in *Bacillus* Species

*Bacillus* species produce and secrete a large number of useful proteins and metabolites (Zukowski (1992) "Production of commercially valuable products," In: Doi and McGlouglin (eds.) *Biology of Bacilli: Applications to Industry*, Butterworth-Heinemann, Stoneham, Mass., pp. 311-337). The most common *Bacillus* species used in industry are *B. licheniformis, B. amyloliquefaciens*, and *B. subtilis*. Because of their GRAS (generally recognized as safe) status, strains of these *Bacillus* species are natural candidates for the production of proteins utilized in the food and pharmaceutical industries. Important production enzymes include α-amylases, neutral proteases, and alkaline (or serine) proteases.

Published U.S. application 2012/0183995 discloses methods and compositions for the improved expression and/or secretion of proteins of interest in *Bacillus*.

Expression in *Corynebacterium glutamicum*

Date et al. (2006) *Lett Appl Microbiol.* 42(1): 66-70.

Expression in *Pseudomonas fluorescens*

Retallack (2011) *Protein Expression and Purification* 81:157-65.

Expression in Eukaryotes

Yeasts and Other Fungi

Cregg et al. (2000) *Mol. Biotechnol.* 16(1): 23-52.

Malys et al. (2011) *Methods Enzymol.* 500:197-212.

Expression in Plant Cells

Hellwig et al. (2004) *Nature Biotechnology* 22(11):1415-1422 comprehensively reviews the field of plant cell cultures for the production of recombinant proteins. The authors note that suspension cell cultures have been prepared from several different plant species, including *Arabidopsis thaliana, Taxus cuspidata, Catharanthus roseus*, and domestic crops such as tobacco, alfalfa, rice, tomato, and soybean. They also point out that some researchers focus on plants with a high protein content, for example soybean and lupin, assuming that these might more readily facilitate higher protein expression levels.

Hempel et al. ((2011) "Algae as Protein Factories: Expression of a Human Antibody and the Respective Antigen in the Diatom *Phaeodactylum tricornutum*", *PLoS ONE* 6(12): e28424. doi:10.1371/journal.pone.0028424) provides an example of the use of an algal cell, *Phaeodactylum tricornutum*, to produce a monoclonal human IgG antibody against the Hepatitis B surface protein and the respective antigen. This reference further discusses the potential of algae as an efficient low cost and $CO_2$-neutral expression system, exhibiting fast growth rates without the risk of human pathogenic contaminations. The authors note current investigations on the use of the green alga *Chlamydomonas reinhardtii* as an expression system.

Expression in Insect and Mammalian Cells

Baculovirus-Infected Insect Cells

Baculovirus-infected insect cells such as the Sf9, Sf21, and Hi-5 strains can be used to express large quantities of glycosylated proteins that cannot be expressed using *E. coli* or yeasts. Genes are not expressed continuously because infected host cells eventually lyse and die during each infection cycle (Yin et al. (2007) *Journal of Biotechnology* 127:335-347).

Non-Lytic Insect Cell Expression

Non-lytic insect cell expression is an alternative to the lytic baculovirus expression system. In non-lytic expression, vectors are transiently or stably transfected into the chromosomal DNA of insect cells for subsequent protein expression (Dyring (2011) *Bioprocessing Journal* 10 (2011) 28-35; Olczak and Olczak (2006) *Analytical Biochemistry* 359 (2006) 45-53). This is followed by selection and screening of recombinant clones (McCarroll and King (1997) *Current Opinions in Biotechnology* 8:590-594). The non-lytic system has been used to give higher protein yield and quicker expression of recombinant proteins compared to baculovirus-infected cell expression (Olczak, supra). Cell lines used for this system include Sf9, Sf21 from *Spodoptera frugiperda* cells, Hi-5 from *Trichoplusia ni* cells, and Schneider 2 cells and Schneider 3 cells from *Drosophila melanogaster* cells (Dyring, supra; McCarroll and King, supra). With this system, cells do not lyse, and several cultivation modes can be used (Dyring, supra). Additionally, protein production runs are reproducible (Dyring, supra; Olczak and Olczak, supra). This system yields a homogeneous product.

Kost et al. (2005) *Nat. Biotechnol.* 23(5):567-75.

Rosser et al. (2005) *Protein Expr. Purif.* 40(2):237-43.

Lackner et al. (2008) *Anal. Biochem.* 380(1):146-8.

Expression in Animal Cells

Currently, about 60-70% of all recombinant protein pharmaceuticals are produced in mammalian cells, and it is estimated that several hundred clinical candidate proteins are under development. Many of these are expressed in immortalized Chinese hamster ovary (CHO) cells, while other cell lines, such as those derived from mouse myeloma (NSO), baby hamster kidney (BHK), human embryo kidney (HEK-293), and human retinal cells have gained regulatory approval for recombinant protein production (F. M. Wurm (2004) *Nature Biotechnology* 22(11):1393-1398). This reference discusses various aspects of recombinant protein expression in mammalian cells, including the design of expression vectors for DNA delivery, and cell culture.

Expression in Protozoal Cells

The eukaryotic protozoan *Leishmania tarentolae* (non-pathogenic strain) expression system, available from Jena Bioscience as the LEXSY (*Leishmania* expression system) system, allows stable and lasting production of proteins at high yield, in chemically defined media. Produced proteins exhibit fully eukaryotic post-translational modifications, including glycosylation and disulfide bond formation.

Examples of specific host cells useful in the present invention include the following. These listings should not be construed to be limiting as other host cells known in the art are also useful in the present methods, and are encompassed by the present invention.

TABLE 1

References Disclosing *E. coli* Strain Genomic Sequences

| Table Entry Number | *E. coli* Strain Number | Reference (Source of Genomic Sequence) | Genome Size (Mb) |
|---|---|---|---|
| 1 | *E. coli* K-12 | Blattner FR, et al. *Science* 1997 Sep. 5; 277(5331): 1453-62. | 4.639 |
| 2 | *E. coli* MG1655 | Blattner FR, et al. *Science* 1997 Sep. 5; 277(5331): 1453-62. | 4.639 |
| 3 | *E. coli* BL21 (DE3) | Jeong Hm et al. *J Mol Biol* 2009 Dec. 11; 394(4): 644-52 | 4.56 |
| 4 | *E. coli* DH10B | Durfee et al. *J Bacteriol.* 2008 Apr.; 190(7): 2597-606 | 4.69 |

TABLE 2

References Disclosing *B. subtilis* Strain Genomic Sequences

| Table Entry Number | *B. subtilis* Strain Number | Reference (Source of Genomic Sequence) |
|---|---|---|
| 1 | *B. subtilis* 168 | Barbe et al. *Microbiology.* 2009 Jun.; 155(Pt 6): 1758-75 |
| 2 | *B. subtilis* BSn5 | Deng et al. *J Bacteriol.* 2011 Apr.; 193(8): 2070-1 |

In Tables 3 and 4, the cited genomic sequence reference is for the permanent curation of the National Center for Biotechnology Information (NCBI). Since eukaryotic cells have multiple chromosomes, their genomic sequences are often spread across multiple publications that each address a specific chromosome or section of a chromosome. NCBI curates this information and compiles it under their permanent Entrez Gene database.

TABLE 3

References Disclosing *S. cerevisiae* Strain Genomic Sequences

| Table Entry Number | *S. cerevisiae* Strain Number | Reference (Source of Genomic Sequence) |
|---|---|---|
| 1 | *S. cerevisiae* S288c | NCBI-Entrez Gene, *Nucleic Acids Res.* 2011 Jan.; 39(Database issue): D52-7 |
| 2 | *S. cerevisiae* AWRI796 | NCBI-Entrez Gene, *Nucleic Acids Res.* 2011 Jan.; 39(Database issue): D52-7 |

TABLE 4

References Disclosing *K. pastoris* Strain Genomic Sequences
(*K. pastoris* was formerly known as *Pichia pastoris*)

| Table Entry Number | *K. pastoris* Strain Number | Reference (Source of Genomic Sequence) |
|---|---|---|
| 1 | *K. pastoris* CBS7435 | Kuberl A, et al. *J Biotechnol* 2011 |
| 2 | *K. pastoris* GS115 | NCBI-Entrez Gene, *Nucleic Acids Res.* 2011 Jan.; 39(Database issue): D52-7 |

TABLE 5

References Disclosing CHO Cell Strain Genomic Sequences

| Table Entry Number | CHO Cell Strain Number | Reference |
|---|---|---|
| 1 | CHO-K1 | Puck TT, et al. *J. Exp. Med.* 108: 945-956, 1958. Xu, et al. *Nature Biotechnology* 29, 735-741 (2011) |

Human embryonic kidney (HEK) cells have 4.5 kb of adenovirus 5 DNA in addition to the human genome. This information can also be found in the NCBI Entrez Gene Database.

TABLE 6

References Disclosing HEK Cell Strain Genomic Sequences

| Table Entry Number | HEK Cell Strain Number | Reference (Source of Genomic Sequence) |
|---|---|---|
| 1 | HEK 293 | NCBI-Entrez Gene, *Nucleic Acids Res.* 2011 Jan.; 39(Database issue): D52-7 |

The following examples are provided to illustrate various aspects of the present invention, and should not be construed as limiting the invention only to these particularly disclosed embodiments. The materials and methods employed in the examples below are for illustrative purposes, and are not intended to limit the practice of the present invention thereto. Any materials and methods similar or equivalent to those described herein can be used in the practice or testing of the present invention.

Example 1

Identification of Host Cell Proteins Associated With a Specific Product, Histidine-Tagged Green Fluorescent Protein, as a Comparative Example This comparative example demonstrates the identification of proteins of the 120 mM imidazole fraction (Ni(II) IMAC) and subsequent gene deletions. It demonstrates how to eliminate host cell contaminants for a specific target recombinant product, Green Fluorescent Protein (GFPuv), extended by a histidine-rich affinity tag ($His_6$-GFP). $His_6$-GFP elutes similarly to other histidine-tagged proteins found in the literature. While this example discloses three gene deletions that, in principle, would enhance the purity of the desired product, the knockouts of cyoA, adhP, and yfbG and their subsequent lack of expression does not favorably impact column capacity. These three proteins are insignificant in the metalloproteome of *E. coli*. Thus, no changes to the separatome are disclosed that lead to an overall increase in separation efficiency. The text of this example is an annotated version of the inventors' work described in Liu et al. (2009) *J. Chromatog. A* 1216:2433-2438.

Strains, Plasmids, and Growth Conditions

*Escherichia coli* BL21 DE3 expressing GFPuv tagged with ($His_6$) (SEQ ID NO:1) were constructed using basic molecular biology techniques. PCR primers F (5'-GCC AAGCTTGTGGCATCATCATCCGCATATGAGTAAAG-GAGAAGAACTTTTC-3') (SEQ ID NO:2) and R (5'-TTG GAATTCATTATTTGTAG AGCT-3') (SEQ ID NO:3) containing Hind III and EcoRI sites (underlined correspondingly), were used to amplify and extend GFPuv. These enzymes were used to digest the PCR fragment and the parent plasmid. T4 DNA ligase was then used to construct a new vector that was built from the PCR-extended gene and the major part of the pGFPuv plasmid. Transformants were selected in LB agar containing 50 µg/ml ampicillin. E. coli cells were grown in Luria-Bertani (LB) overnight and inoculated in a 2-liter flask containing 500 ml M9 supplemented with 10 g/L glucose such that the initial $A_{660}$ was 0.1. To express $His_6$-GFPuv, 4% inoculations of overnight cultures were made in 500 mL LB and induced with 1 mM of IPTG after 1-2 hours. Fermentations were carried out at 37° C. and the agitation speed of the shaker was set at 200 rpm. Cell pellets were collected by centrifugation at 5000 g and frozen at −80° C. before cell lysis.

Sample Preparation and Chromatography

Cell pellets were suspended in 20 ml 1× native purification buffer (50 mM $NaH_2PO_4$, pH 8.0; 500 mM NaCl) combined with 100 µl Triton X-100, 80 µl 100 mM $MgCl_2$, 20 µl phenylmethylsulphonyl fluoride (PMSF) and 100 µl 100 mg/mL lysozyme. The mixture was sonicated on ice at 4 W for 30 min using a Vibra cell ultrasonifier (Fisher Scientific, Pittsburgh, Pa., USA), and centrifuged at 5000 rpm for 20 min. The supernatants were collected and passed through a 0.45 µm filter before column loading.

For experiments identifying natural contaminants or to follow the adsorption and elution of $His_6$-GFP, the cleared lysate was applied to 4 ml ProBond nickel-chelating resin in an open column followed by equilibration using 1× native purification buffer (5× native purification buffer, as supplied with the resin, is comprised of 250 mM NaH2PO4, pH 8.0. 2.5 M NaCl). Step elutions were carried out with native purification buffer with the following imidazole concentrations: 60 mM, 80 mM, 100 mM, 120 mM, and 200 mM. This was followed by a 500 mM EDTA elution. The elution volumes for each step were 24 ml, or 6 column volumes (CVs), and applied at an approximate flow rate of 0.5 ml/min. Fractions were collected and measured for protein concentration with a BCA Protein Assay Kit (Pierce, Rockford, Ill., USA) and/or assayed for GFPuv in triplicate with a Tecan Infinite M200 96-well plate reader with excitation/emission spectra set to 395/509 nm.

SDS-PAGE and Mass Spectrometry.

Sodium dodecyl sulfate polyacrylamide gel electrophoresis (SDS-PAGE) was performed for 6 hours at 100 V. Gels were stained with Coomassie Blue. The Genomics and Proteomics Core Laboratories at the University of Pittsburgh performed the protein identification. To account for the experimental accuracy of the measurement, three spots were excised from each band and each digested with trypsin. Peptides were separated by liquid chromatography (LC), then identified by tandem mass spectrometry (MS/MS) fragmented by collision-induced dissociation. MASCOT v2.1 (Matrix Science, Boston Mass. USA) was used to match LC/MS data with E. coli proteins. For positive identification, spectral data from each of the three spots matched.

Functional Prediction of Identified Proteins in 120 mM Elution Fraction.

Functional classification of all identified proteins was based on the Profiling of Escherichia coli chromosome (PEC) database (Hashimoto et al. (2005) Molecular Microbiology 55: 137-149).

Construction of Knockout Mutants.

All the knockout mutants of this Example were generated with the same deletion system according to the manual accompanying the Quick and Easy E. coli Gene Deletion Kit (Gene Bridges, Heidelberg, Germany). This kit uses plasmid pRedET to facilitate homologous recombination events. During the progression of the work, a triple mutant of BL21 (ΔcyoAΔyfbGΔadhP) was constructed through a series operation consisting of recombination, selection with kanamycin, confirmation, and removal of the selection marker using flipase recognition site (FRT flanked kanamycin gene).

Southern Blot Analysis

DNA probes used for Southern hybridization were prepared from PCR-amplified fragments. Probes were labeled according to the manual of Amersham Gene Images Random Prime Labeling Kit (GE Healthcare). Genomic DNA was isolated from knockout mutants using standard protocols. DNA samples were digested with Bam HI, separated by electrophoresis on 1% agarose gels, transferred to Amersham Hybond-N+ membranes (GE Healthcare), and then baked at 80° C. for 2 hours. The probes were hybridized to these blots and detected according to the protocol of the Gene Images ECL Detection Kit (GE Healthcare).

SDS-PAGE Evaluation of CyoA, YfbG and AdhP Knockout in Mutant Strains.

Cell preparations of BL21, mutants, and chromatography fractions were evaluated by SDS-PAGE. Approximately 15 µg sample/well were loaded into a 12% acrylamide gel.

Identification of Knockout Candidates and Confirmation of their Deletion

Figure 3:
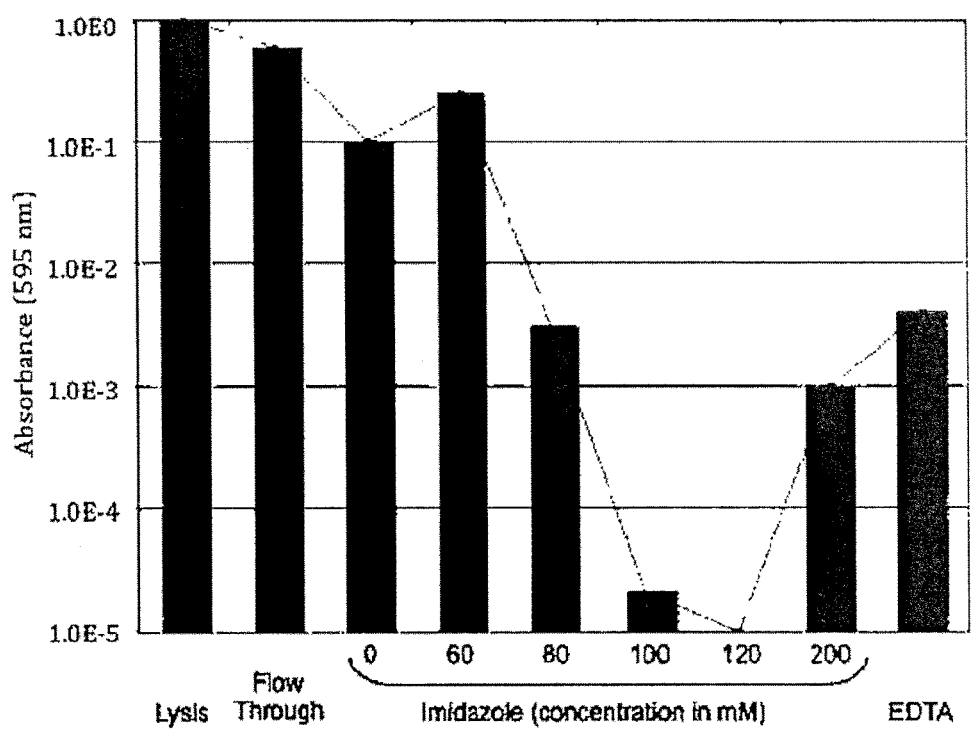
FIG. 3 shows the distribution of proteins contained within various IMAC fractions that elute from a Ni(II) column. In particular, note the low concentration of host cell proteins within the 120 mM fraction.

A total extract of E. coli protein was loaded to the ProBond nickel-chelating column using 1× native purification buffer (5× native purification buffer, as supplied with the resin, is comprised of 250 mM NaH2PO4, pH 8.0. 2.5 M NaCl). Step elutions were carried out with native purification buffer with the following imidazole concentrations: 60 mM, 80 mM, 100 mM, 120 mM, and 200 mM. FIG. 3 shows the protein concentrations in each fraction normalized to the total protein used for column loading. The bar graph indicates order of magnitude changes in the total protein encountered with each imidazole challenge. Note that the elution fraction containing the 120 mM imidazole fraction contained the least amount of protein. Coincidentally, this fraction that contains low host cell protein is also the fraction where $His_6$-GFPuv elutes.

Figure 4:
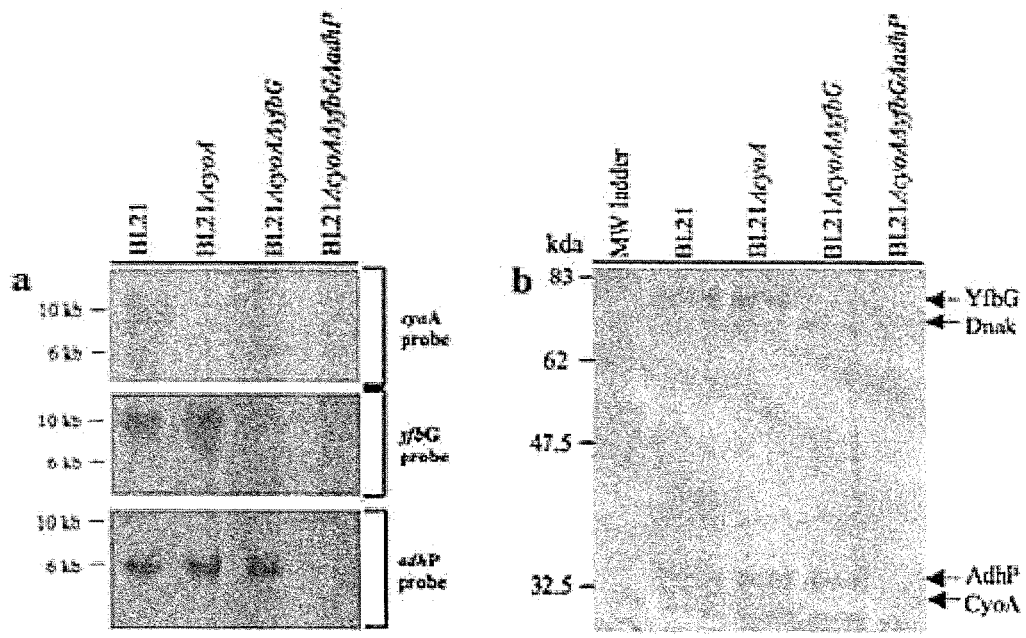
FIG. 4 shows a Western blot (a) and protein gel (b) that indicate lack of expression of gene products of yfbG, adhP, and cyoA. Lack of expression is indicated by absence of spot or band.

SDS-PAGE and LC-MS/MS were used to identify the cellular proteins present in the concentrated sample of pooled 120 mM imidazole elution fractions. A total of 18 proteins were identified (Table 7), with cyoA, yfbG, and adhP selected for deletion due to lack of essentiality. Southern blot analysis and gel electrophoresis indicated lack of expression of the three gene products cyoA, yfbG, and adhP. FIG. 4 shows this confirmation due to lack of spots associated with positive hybridization and bands of the molecular weights of these products, respectively.

TABLE 7

| Proteins eluted at 120 mM from a Ni(II)-NTA column |
|---|
| dnaK |
| yfbG |
| adhP |
| cyoA |
| rplB |
| slyD |
| nagD |
| ahpC |
| rpsG |
| rplO |
| rpsE |
| rplM |

TABLE 7-continued

Proteins eluted at 120 mM from a Ni(II)-NTA column

Fur
Hypothetical protein
ECs2542 rplJ
rpsL
Hns
rplL

These results demonstrate that it is possible to apply a limited set of data and to produce a knockout strain capable of enhancing the purity of a recombinant peptide, polypeptide, or protein. It is used as a comparative example to illustrate the lack of a rigorous methodology to identify specific changes to the host cell that lead to an altered separatome capable of broadly improving separation efficiency, and column capacity in particular, regardless of desired recombinant product.

Example 2

Construction of the Ion Exchange Separatome of *E. coli* and its Use to Design and Build Novel Host Strains for a Common Chromatography Resin This example describes the process by which a separatome is constructed for a chromatography resin and subsequently used to guide modifications to *E. coli* to increase chromatographic efficiency. It begins by describing how data are acquired by fractionating an extract derived from fed batch growth over a DEAE ion exchange bed, and continues by constructing the separatome—a data structure that includes information on the genes responsible for identified proteins coupled to a quantitative scoring to rank order molecular biology efforts that lead to a reduced separatome. Finally, construction of example strains is described, concluding with information regarding high priority strain modifications necessary for significant gains in separation efficiency through their deletion, modification, or inhibition.

Cloning Strains and Vectors

*E. coli* strain MG1655 (K-12 derivative) was selected as the base strain for cell line modification because of its widespread use and lack of commercial license. Its genotype is F⁻ lambda⁻ rph⁻¹, meaning that it lacks an F pilus, the phage lambda, and has al 5 codon frame-shift as result of the rph 1 bp deletion (Yale University. *E. coli* Genetic Stock Center Database. 2013). This frame-shift interrupts the pyrE gene and reduces pyrimidine levels (Jensen et al. (1993) *Journal of Bacteriology* 175(11):3401-7).

Plasmid pKD46 was used as part of the k-red recombination system. This plasmid is ampicillin resistant and replication is temperature sensitive. For plasmid maintenance, growth is at 30° C. and the plasmid can be removed by growth at 37° C. without antibiotic pressure. The plasmid encodes for lambda Red genes exo, bet, and gam, and includes an arabinose-inducible promoter for expression (Datsenko et al. (2000) *PNAS* 97(12):6640-5). The plasmid was provided in conjunction with MG1655 from the Yale *E. Coli* Genetic Stock Center (New Haven, Conn.).

Expression Strains and Vectors

*E. coli* strain BL21 (DE3) was used for initial cell culture and cell lysate preparation. Its genotype is F-ompT hsdSB (rB-, mB-) gal dcm (DE3). The strain and genotype was provided by Novagen (EMD-Millipore/Merck). The cell line was transformed with a recombinant pGEX plasmid provided by Dr. Joshua Sakon (Department of Chemistry, University of Arkansas). This plasmid, pCHC305, contains the genetic information for the recombinant fusion protein, glutathione-S-transferase—parathyroid hormone—collagen binding domain (GST-PTH-CBD, 383 amino acids).

Storage Strains and Vectors

For storage of DNA constructs, *E. coli* strain DH5α was selected. Its genotype is F-, Δ(argF-lac)169 φ80dlacZ58 (M15) ΔphoA glnV44(AS)8λ-deoR481 rfbC gyrA96 (NalR)1 recA1 endA1 thiE1 hsdR17. DH5 is a non-mutagenized derivative of DH1, which transforms more efficiently due to a deoR mutation. The recA mutation eliminates homologous recombination and minimizes undesired modification to stored plasmids. pUC19 was used as a DNA storage vector. It is a high copy number plasmid that carriers ampicillin resistance. This plasmid was provided in conjunction with DH5α from the Yale *E. Coli* Genetic Stock Center (New Haven, Conn.).

Liquid Growth Media

M9 medium was used where a minimal defined medium was required. M9 Medium was made in 3 separate stock solutions: glucose solution (500 g/L), trace elements (2.8 g of FeSo4-7H2O, 2 g of MnCl2-4H2O, 2.8 g off CoCl2-7H2O, 1.5 g of CaCl2-2H2O, 0.2 g CuCl2-2H2O, 0.3 g of ZnSO4-7H2O), and 5×M9 (75 g of K2HPO4, 37.5 g of KH2PO4, 10 g of citric acid, 12.5 g of (NH4)2SO4, 10 g of MgSO4-7H2O). Each of these components must be autoclaved individually to minimize salt precipitation. To prepare 1 L of M9, 14.5 ml of the glucose solution is mixed with 1 ml trace element solution, 200 ml of 5× M9, and enough water to bring the final volume up to 1 L (approximately 784.5 ml).

Where rich medium was required, Luria-Burtani (LB) Medium was used. LB powder was purchased from Difco and was prepared per the manufacturer's instructions: 20 g LB powder per 1 L of MILLI-Q® water (ultrapure water in agreement with the quantitative specifications of Type I water as described in ISO 3696, ASTM D1193, and of EP and USP Purified Water, as well as the CLSI®-CLRW).

Solid Growth Media

Solid M9 medium was prepared as previously described for liquid M9 with the addition of agar to the water and concentrated M9 solution prior to autoclaving. To prepare 500 ml of M9 agar, 7.5 g agar, 100 ml of 5×M9 solution, and 300 ml of water are mixed and autoclaved. Added to this is 7.25 ml sterile glucose solution (700 g/L), 500 µl trace elements, and enough sterile water to bring the final volume up to 500 ml. The other solid medium used was LB agar, which was prepared the same as the LB liquid medium described earlier plus the addition of 7.5 g agar per liter.

Fed-Batch Cultivation

Fed-batch cultivation was used to prepare the cell lysate for use in downstream protein purification and identification of natively expressed proteins. The cell line used was BL21 pCHC305. To begin fermentation, a single colony was isolated from a LB ampicillin agar plate and transferred to a 5 ml culture tube containing liquid LB plus 150 µg/ml ampicillin. This culture tube was allowed to incubate overnight at 37° C. After overnight growth, the 5 ml culture tube is supplemented with 100 ml of M9 with ampicillin and allowed to grow at 37° C. for six to eight hours. This 100 ml culture is then centrifuged at 4750 rpm for 25 minutes (Beckman Coulter Allegra) and re-suspended in 50 ml of fresh M9 medium with 150 µg/ml ampicillin. This culture is used as the inoculant for the fed-batch growth. The 3-liter Applikon bioreactor (Foster City, Calif.) contained 1 liter of M9 plus 150 m/mlampicillin and 1 ml silicone anti-foam.

The Applikon was equipped with BioXpert Advisory software from Applikon, an Applisense pH probe, and a dissolved oxygen probe. To maintain proper dissolved oxygen, the reactor was supplemented with a compressed oxygen cylinder with a controllable flow rate. To insure effective gas dispersal, the culture was initially stirred at 750 rpm and was later increased to 1000 rpm based on cell density. Adjustments in oxygen delivery were made as necessary during the process to ensure that the dissolved oxygen concentration did not drop below 35%. The pH was maintained at approximately 6.8 (with a range of 6.75 to 7) during the cultivation by adding 7M $NH_4OH$ as needed. Temperature was maintained at 37° C. using a heating jacket and cooling loop. Optical densities were monitored using a BUGEYE™ optical density probe (BUGLAB®, Foster City, Calif.) and a DU800 Beckman Coulter spectrophotometer (Brea, Calif.). BUGEYE™ is a non-invasive optical biomass measuring device for measuring biomass through the side wall of a shake flask using a handheld sensor, described in U.S. Pat. No. 8,405,033. A linear correlation for the BUGEYE™ response to the actual optical density (OD) as measured by the spectrophotometer was determined for each individual experiment.

The fed-batch fermentation process has two phases, a batch phase and a feeding phase. In the batch phase, the culture uses only the carbon sources provided in the media at the start of the cultivation and no nutrients are fed to the reactor. This phase lasts approximately 7-8 hours, depending on the lag phase of the culture and how rapidly the culture grew on the initial carbon substrate. The shift from batch phase to feeding phase can be determined by two indicators, a rise in pH and a sharp decline in oxygen concentration, which indicate that the initial carbon substrate has been depleted. In the fed-batch experiments, these two events occur simultaneously and are displayed by the Applikon software. The feeding profile used for fermentation experiments is based on that of a collaborator (McKinzie Fruchtl) and was originally proposed by Korz et al. (1995) *Journal of Biotechnology* 39(1):59-65 and Lee et al. (1996) *Trends in Biotechnology* 14(3):98-105. A feeding profile was programmed into the Applikon software that mimics the exponential feed based on substrate concentrations.

An exponential fed-batch fermentation method commonly used to pre-determine the amount of glucose that should be fed into the reactor to achieve a certain growth rate was proposed by Korz et al. and Lee et al., supra:

$$M_S(t) = F(t)S_F(t) = \left(\frac{\mu}{Y_{X/S}} + m\right)X(t)V(t) = \left(\frac{\mu}{Y_{X/S}} + m\right)X(t_F)V(t_F)\exp^{\mu(t-t_F)}$$

where $M_S$ is the mass flow rate (g/h) of the substrate, F is the feeding rate (1/h), $S_F$ is the concentration of the substrate in the feed (g/l), $\mu$ is the specific growth rate (1/h), $Y_{X/S}$ represents the biomass on substrate yield coefficient (g/g), m is the maintenance coefficient (g/g h), and X and V represent the biomass concentration (g/l) and cultivation volume (l), respectively. The yield coefficient for *E. coli* on glucose is generally taken to be 0.5 g/g (Korz et al., supra; Shiloach et al. (2005) *Biotechnology Advances* 23(5):345-57). The maintenance coefficient is often 0.025 g/g h (Korz D J et al., supra. This equation has been widely adapted for fed-batch fermentation processes, as exponential feeding allows cells to grow at a constant rate (Kim et al. (2004) 26(3):147-50).

During fed-batch fermentation, the cells were left un-induced to prevent the addition of the recombinant protein to the native protein pool. The fermentation was allowed to grow for a total of 24 hours from inoculation to harvest. At the end of the fermentation process, cells were harvested from the reactor by pumping the reactor contents into centrifuge bottles. The reactor contents were then centrifuged at 12,000×g for 30 minutes at 5° C. (Beckman Coulter Avanti, JLA-10.500 fixed angle rotor) to separate the cell pellet from the media. The pellet was separated into four 50 ml conical bottom tubes for storage at −20° C.

Lysate Preparation

One of the 50 ml pellets (58.9 g) was re-suspended in 150 ml of 25 mM Tris buffer, pH 7. To enable cell lysis, 2 mg/ml lysozyme were added to the mixture. In addition, 1 mM phenylmethylsulphonyl fluoride (PMSF), 20 µg/ml aprotinin, and 1 mM ethylenediamine-tetraacetic acid (EDTA) was added to minimize protein degradation. The mixture was then incubated on ice with stirring for 30 minutes to lyse the cells. The mixture was then centrifuged at 50,000×g (Beckman Coulter Avanti, JA-25.50 fixed-angle rotor) for 30 minutes at 5° C. to separate the proteins from the cell debris.

The proteins in the supernatant were carefully pipetted out of the centrifuge tubes, to minimize contaminants from the insoluble fraction, and were clarified by syringe filtration through 0.45 µm cellulose acetate. Lastly, the total protein concentration of the cell lysate was determined by using a Bio-Rad DC Protein Assay which is a detergent compatible colorimetric assay that is read by spectrophotometer at 750 nm (Beckman Coulter DU 800 HP). Bovine serum albumin standards were used to determine the baseline correlation between protein concentration and absorbance at 750 nm.

Fast Protein Liquid Chromatography

Fast protein liquid chromatography (FPLC) was used to separate the natively expressed proteins into groups based on the salt concentration at which they elute, which correlates to their surface charge. The chromatography was performed using an Amersham ÄkTA FPLC. The system consists of dual syringe pumps (P-920), gradient mixer, a monitor (UPC-900) for UV (280 nm), pH and conductivity, a fraction collector (Frac-900) and UNICORN® V3.21 data collection and archive software.

Resin

For the initial database development, diethylaminoethyl cellulose (DEAE) was selected as the ion exchange (IEX) resin due to its prevalence of use in industrial manufacturing. Specifically, the column used was a 1 ml HiTrap DEAE FF from GE Healthcare. DEAE is a weak anion exchanger, meaning that it is a positively charged matrix with a narrow working pH of 2-9 (GE Healthcare. Instructions 71-5017-51 AG HiTrap ion exchange columns. 1-24.).

Buffer Composition 25 mM Tris buffer, pH 7, was selected for all of the FPLC purification steps. The loading buffer contained 10 mM NaCl to minimize non-specific binding (Buffer A). The elution buffer contained 1M NaCl, which is sufficient to desorb bound proteins (Buffer B).

Column Loading Conditions

Prior to loading the column, the system was washed with buffer A until equilibrium was achieved (roughly 10 ml). At this point, all system monitors were base-lined. The column was loaded at 10% breakthrough as per industry standard. The amount of total lysate to be applied to the column to achieve this breakthrough was determined as follows. According to GE Healthcare, the dynamic binding capacity (DBC) of HiTrap DEAE FF is 110 mg HSA (human serum albumin)/ml solvent (resin). This number gives the amount of protein that can be bound per milliliter of resin. The next step was to determine what percentage of the native proteins bound to the DEAE resin at pH 7. To do this, 5 ml of lysate was loaded on the column and washed with 10 ml of buffer A. The flow-through was collected in a single fraction. The column was then washed with the buffer B and the resulting flow-through was collected. Both fractions were then analyzed for their total protein concentration using the previously mentioned Bio-Rad assay. The amount of lysate (ml) to load onto the column was determined by the following equation:

$$\text{lysate (ml)} = \frac{DBC * (1 + \%_{BT}) * V_C}{\%_{bound} * C_l}$$

where DBC is the dynamic binding capacity of the resin (mg/ml), $\%_{BT}$ is the desired percent breakthrough, $V_c$ is the volume of the column (ml), $\%_{bound}$ is the percent of the total lysate that binds to the resin, and $C_1$ is the protein concentration of the lysate (mg/ml).

The column was loaded at 1 ml/min and then washed with 10 column volumes (CV) of buffer A to remove any unbound proteins. The unbound fraction was collected for later analysis.

Column Elution Conditions

To identify where the bulk of the bound proteins eluted, the proteins were desorbed through roughly 100 mM salt steps from 10 mM to 1M. This process allows for the identification of the priority salt fractions that need to be spaced out into smaller steps for later analysis.

TABLE 8

10% Elution Steps

| Step # | % B | NaCl (mM) | Step Length (CV) |
|---|---|---|---|
| wash | 0% | 10 | 10 |
| 1 | 10% | 109 | 5 |
| 2 | 20% | 208 | 5 |
| 3 | 30% | 307 | 5 |
| 4 | 40% | 406 | 5 |
| 5 | 50% | 505 | 5 |
| 6 | 60% | 604 | 5 |
| 7 | 70% | 703 | 5 |
| 8 | 80% | 802 | 5 |
| 9 | 90% | 901 | 5 |
| 10 | 100% | 1000 | 5 |
| clean | 100% | 1000 | 5 |

The flow rate was maintained at 1 ml/min and the pressure limit was set to 0.5 MPa for the duration of the experiment. During elution, all fractions were collected and immediately stored at 2° C. to reduce protein degradation. After all of the proteins have been desorbed in the 1000 mM step, the fraction collector is stopped and the column is cleaned with buffer B to ensure all proteins have been desorbed and washed out of the column. The column is then washed with sufficient buffer A to re-equilibrate the column.

For finer focusing on the primary elution windows, smaller 5% steps are used (Table 9). In this instance, the focus was on the 10 mM to 500 mM window.

TABLE 9

5% Elution Steps

| Step # | % B | NaCl (mM) | Step Length (CV) |
|---|---|---|---|
| wash | 0% | 10 | 20 |
| 1 | 5% | 59.5 | 15 |
| 2 | 10% | 109 | 15 |
| 3 | 15% | 158.5 | 15 |
| 4 | 20% | 208 | 15 |
| 5 | 25% | 257.5 | 15 |
| 6 | 30% | 307 | 15 |
| 7 | 35% | 356.5 | 15 |
| 8 | 40% | 406 | 15 |
| 9 | 45% | 455.5 | 15 |
| 10 | 50% | 505 | 15 |
| wash | 100% | 1000 | 20 |

Analytical Assays
Sample Processing

Prior to the samples undergoing further analysis, they were concentrated using a GE Lifesciences VIVASPIN™ 20 (5,000 MWCO). VIVASPIN™ is a centrifugal membrane ultrafiltration sample concentrator employing a semipermeable membrane with a molecular weight cutoff selected by the user for non-denaturing concentration of biological samples by membrane ultrafiltration. Centrifugation is applied to force solvent through the membrane, leaving a more concentrated sample in the upper chamber of the device. This reduced the 20 ml fractions to 2 ml total volume. This was split into two 1 ml samples, one was sent for LC-MS/MS, and the other was kept for SDS-PAGE.

Protein Gels—SDS-PAGE

Sodium dodecyl sulfate-polyacrylamide gel electrophoresis (SDS-PAGE) was used to observe the approximate number of proteins in each FPLC salt fraction and their molecular weight. Prior to SDS-PAGE, the samples were desalted by buffer exchange. To do this, the previously mentioned 1 ml sample of the desired fraction was concentrated in a GE Lifesciences VIVASPIN™ 2 (5,000 MWCO) and re-suspended in 25 mM Tris buffer, pH 7. The concentration and re-suspension process was repeated two more times to ensure all salt had been removed. After the last concentration step, the sample was left in its concentrated form to be loaded onto the SDS-PAGE.

A Bio-Rad PROTEAN® II system (large format vertical electrophoresis cell used for common electrophoretic techniques such as SDS-PAGE, native electrophoresis, and agarose gel electrophoresis) was used for the electrophoresis with SDS buffer. The SDS buffer is made as a 10× stock, where the 1× running buffer is 25 mM Tris, 192 mM glycine, and 0.1% SDS at a pH of 8.6. For visualization of the chromatography samples, a 12.5% gel was used. The samples are mixed 5:1 with a 5× loading dye.

Electrophoresis was carried out at 100V until the sample was through the stacking gel, then increased to 140V. Average run time was around 1 hour. Gels were stained using a Coomassie Blue stain (40% methanol, 10% acetic acid and 0.5% Coomassie blue) for 3 hours and then de-stained with a 10% acetic acid and 40% methanol solution. Gel images were captured by scanning on a computer flatbed scanner.

Liquid Chromatography Mass Spectroscopy (LC-MS/MS)

Samples of each FPLC salt fraction were sent to Bioproximity (Chantilly, Va.) for protein identification via liquid chromatography mass spectroscopy (LC-MS/MS). The protocol for the LC-MS/MS was provided by Bioproximity as follows.

Protein Denaturation and Digestion

Prior to digestion, proteins were prepared using the filter-assisted sample preparation (FASP) method (Wiśniewski et al. (2009) 6(5):359-62). Next, the sample was mixed with 8 M urea, 10 mM dithiothreitol (DTT), 50 mM Tris-HCl at pH 7.6 and sonicated briefly. Samples were then concentrated in a Millipore AMICON® Ultra (30,000 MWCO) device (a cellulose membrane centrifugal filter unit for concentrating biological samples) and centrifuged at 13,000×g for 30 mM. The remaining sample was buffer exchanged with 6 M urea, 100 mM Tris-HCl at pH 7.6, then alkylated with 55 mM iodoacetamide. Concentrations were measured using a QUBIT® fluorometer (Invitrogen) for quantitating DNA, RNA, and proteins using fluorescent dyes that emit signals only when bound to specific target molecules. The urea concentration was reduced to 2 M, trypsin was added at a 1:40 enzyme to substrate ratio, and the sample incubated overnight on a THERMOMIXER® temperature-controlled device used for mixing liquids in closed micro- and larger test tubes, and micro test plates (Eppendorf) at 37 C. The AMICON® was then centrifuged and the filtrate collected.

Peptide Desalting

Digested peptides were desalted using C18 stop-and-go extraction (STAGE) tips (Rappsilber et al. (2003) *Analytical Chemistry. American Chemical Society* 75(3):663-70). For each sample, the C18 STAGE tip was briefly activated with methanol, and then conditioned with 60% acetonitrile and 0.5% acetic acid, followed by 2% acetonitrile and 0.5% acetic acid. Samples were loaded onto the tips and desalted with 0.5% acetic acid. Peptides were eluted with a 60% acetonitrile, 0.5% acetic acid solution and dried in a vacuum centrifuge (Thermo Savant).

Liquid Chromatography-Tandem Mass Spectrometry

Peptides were analyzed by LC-MS/MS. LC was performed on an Easy-nanoLC II HPLC system (Thermo). Mobile phase A was 94.5% MILLI-Q® water, 5% acetonitrile, 0.5% acetic acid. Mobile phase B was 80% acetonitrile, 19.5% MILLI-Q® water, 0.5% acetic acid. The 120 min LC gradient ran from 2% B to 50% B over 90 min, with the remaining time used for sample loading and column regeneration. Samples were loaded to a 2 cm×100 um I.D. trap column positioned on an actuated valve (Rheodyne). The column was 13 cm×100 μm I.D. fused silica with a pulled tip emitter. Both trap and analytical columns were packed with 3.5 μm C 18 resin (Magic C 18-AQ, Michrom). The LC was interfaced to a dual pressure linear ion trap mass spectrometer (LTQ Velos, Thermo Fisher) via nano-electrospray ionization. An electrospray voltage of 2.4 kV was applied to a pre-column tee. The mass spectrometer was programmed to acquire, by data-dependent acquisition, tandem mass spectra from the top 15 ions in the full scan from 400-1400 m/z. Dynamic exclusion was set to 30 seconds.

Data Processing and Library Searching

Mass spectrometer RAW data files were converted to MGF (Mascot generic format) using msconvert (Kessner et al. (2008) *Bioinformatics* 24(21):2534-6). Detailed search parameters are printed in the search output XML (extensible markup language) files. All searches required strict cryptic cleavage, up to three missed cleavages, fixed modification of cysteine alkylation, variable modification of methionine oxidation and expectation value scores of 0.01 or lower. Searches used the sequence libraries: UniProt *Escherichia coli* (strain B/BL21-DE3, The UniProt Consortium (2012) *Nucleic Acids Research* 40 (Database issue):D71-5), the common Repository of Adventitious Proteins (cRAP) (*The Global Proteome Machine. Common Repository of Adventitious Proteins,* 2012 Jan. 1) and the given sequence for plasmid product GST-PTH-CBD. MGF files were searched using X!!Tandem (Craig et al. (2004) *Bioinformatics* 20(9): 1466-7) using both the native and k-score (MacLean et al. (2006) *Bioinformatics* 22(22):2830-2) scoring algorithms and by the Open Mass Spectrometry Search Algorithm (OMSSA) (Geer et al. *Journal of Proteome Research* 3(5): 958-64). All searches were performed on Amazon Web Services-based cluster compute instances using the Proteome Cluster interface. XML output files were parsed and non-redundant protein sets determined using MassSieve. Proteins were required to have two or more unique peptides across the analyzed samples with E-value scores of 0.01 or less, 0.001 for X!Hunter and protein E-value scores of 0.0001 or less.

Protein Quantitation

Proteins were quantified the spectral counting method (Liu et al. (2004) *Analytical Chemistry* 76(14):4193-201). This results in a hit count, which is approximate of protein concentration in the sample.

Database Construction
Compilation of Data

The received LC-MS/MS data was imported into Microsoft Access 2010 for data management. The ECOGENE®'s EcoTools Database Table Download (Rudd K E. Database Table Download ECOGENE® 3.0. Department of Biochemistry and Molecular Biology R-629, University of Miami Miller School of Medicine; 2012) was used to supplement the received LC-MS/MS data with additional genomic and proteomic data. The data added were: the protein length (in amino acids), direction of replication (clockwise or counterclockwise), left end position of the gene (in base pairs), right end position of the gene (in base pairs), molecular weight of the protein, common gene name, synonym gene name, protein name, protein function, description, GenBank GI ID (Benson et al. (2013) GenBank. *Nucleic acids Research* 41(Database issue):D36-42) and UniProtKB/Swiss-Prot ID (The Uniprot Consortium (2012) *Nucleic acids Research* 40(Database issue):D71-5). The ECOGENE® Cross Reference Mapping and Download tool was used to Bnum (Blattner number) (Blattner et al. (1997) *Science* 277(5331):1453-62). Microsoft Access was used to build relationships between the various datasets that allowed for searches across the compiled database.

Gene essentiality data were retrieved from Gerdes et al. (2003) *J. Bacteriol.* 185(19):5673-84) which compiles gene essentiality from their own research as well as the Profiling of *E. coli* Chromosome (PEC) database (Hashimoto et al. (2005) *Molecular Microbiology* 55(1):137-49; Kato and Hashimoto (2007) *Molecular Systems Biology* 3(132):132; and Kang Y et al. (2004) *J Bacteriol.* 186(15):4921-30).

Data Manipulation

In order to determine the priority of genes to be deleted, each gene was given a score for each elution window. This score or importance criterion was defined by:

$$importance_i = \sum_j \left[ b_1 \left(\frac{y_{c_j}}{y_{max}}\right) \left(\frac{h_{i,j}}{h_{i,total}}\right) \left(\frac{h_{i,j}}{h_{j,total}}\right) \left(\frac{MW_i}{MW_{ref}}\right)^\alpha \right]_i$$

with the following definitions: $y_{cj}$ and $y_{max}$=concentration of mobile phase eluent in fraction (j) and maximum value, respectively; and $h_{i,j}$ and $h_{i,total}$=the amount of protein (i) in fraction (j) and total bound protein (i), respectively; and $h_{j,total}$=total amount of protein in fraction (j).

In the function given, the score can range from 1 (high) to 0 (low). The summation ranges over the desired elution windows (j) and can be adjusted to cover all of the windows, or target a select few. The first ratio accounts for adsorption strength with $y_{cj}$ being the concentration of the elution solvent (in the case of ion exchange, this is NaCl) and $y_{max}$ being the maximum solvent concentration. The second ratio accounts for adsorption specificity with $h_{i,j}$ being the protein concentration in the window, over the total protein concentration in all windows ($h_{i,total}$). For proteins that elute in only one window, this value will be 1, where proteins that elute in multiple windows will have a lower ratio. The third ratio describes the relative amount a protein has in a given fraction, and the forth ratio accounts for the possibility of steric hindrance.

The second and third equations define how much capacity is recovered when the protein is removed, and the overall capacity recovery as one modifies, deletes, or inhibits n genes, respectively $$\text{recovery } potential_i = \frac{h_{i,total}}{h_{total,ms}}$$

and $$\text{capacity recovery} = 100\% \times \sum_{i=1}^{n} \text{recovery } potential_i$$

Homologous Recombination
Removal of Genomic thyA

Figure 5:
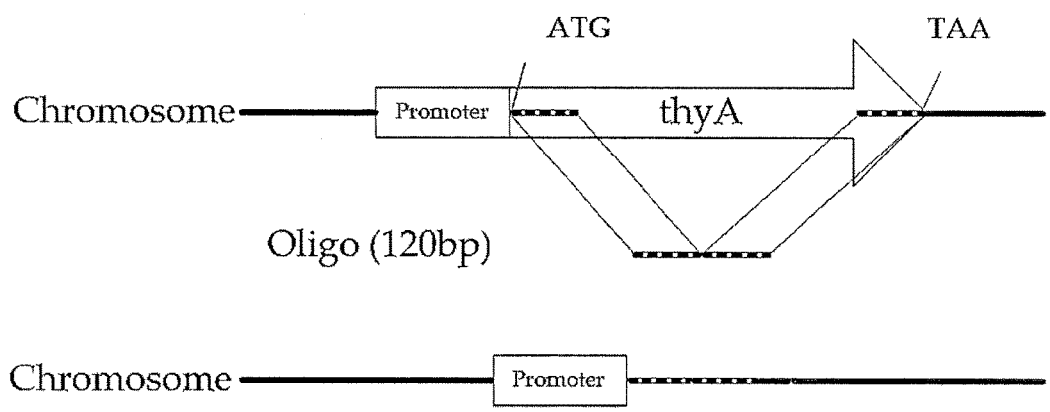
FIG. 5 shows removal of thyA prior to homologous recombination.

Flexible Recombineering Using Integration of thyA (FRUIT) as described by Stringer et al. ((2012) *PloS one.* 7(9):e44841), a modification of the Datsenko λ-Red homologous recombination system (Datsenko et al. (2000) *PNAS* 97(12):6640-5), was used to delete the targeted genes from the genome of *E. coli* strain MG1655. The method begins by creating an MG1655 ΔthyA strain by swapping the gene for an oligonucleotide designed to have 60 bp of homology at the beginning and the end of the thyA gene. FIG. 5 shows the process by which this deletion is performed.

This oligonucleotide was ordered as two linear single stranded DNA fragments from Integrated DNA Technologies (Coralville, Iowa). The fragments were hydrated in Qiagen EB buffer (Tris, pH 8, 1.4M NaCl) and mixed in a 1:1 ratio. The mixture was then placed in a MJ Research PTC-200 DNA Engine thermocycler that was programed to heat to 98° C. and then drop the temperature by 2° C. every 30 seconds until it reached 25° C.

To Delete thyA

MG1655:pKD46 was cultured overnight at 30° C. in LB plus ampicillin (100 µg/ml). The following morning, the overnight was sub-cultured 1:100 into 5 ml of fresh LB-ampicillin with 0.2% L-arabinose and allowed to grow for approximately three hours, until the culture reached an $OD_{600}$ (HP DU800) of 0.6 to 0.8. All proper controls were also taken to validate the recombination event. To prepare the cells for electroporation, the 5 ml induced culture was split into four 1 ml aliquots and moved to 1.5 ml microfuge tubes. The final 1 ml was refrigerated for later analysis or for further sub-culturing. The microfuge tubes were centrifuged for 60 seconds at 14,000 rpm in a cooled (placed in refrigerator, 2° C.) compact bench-top microfuge centrifuge (Eppendorf, MINISPIN®). The supernatant was discarded by gently pouring off the liquid and then the pellet was placed on ice. The pellet was then re-suspended in 1 ml of chilled distilled/deionized water ($ddH_2O$) and then centrifuged again. This process was repeated once more. After the supernatant is poured off the final time, there is roughly 100 µl of liquid left in the tube. Next, the cells are re-suspended in the remaining fluid and kept on ice. To this, the prepared linear fragment is added, in this case the thyA deletion template, various concentrations, usually ranging from 200-1000 nmol. This mixture was then pipetted into chilled sterile electroporation cuvettes (Bio-Rad, 0.1 cm gap). The sample was the electroporated using a Bio-Rad MICRO-PULSER™ set to Ec1 (*E. coli*, 0.1 cm cuvette, 1.8 kV, one pulse). The Bio-Rad MICROPULSER™ is an apparatus used for the electroporation of bacteria, yeast, and other microorganisms where a high voltage electrical pulse is applied to a sample suspended in a small volume of high resistance media, consisting of a pulse generator module, a shocking chamber, and a cuvette with incorporated electrodes. Next, 1 ml of LB containing ampicillin (50 µg/ml), thymine (100 µg/ml) and trimethoprim (20 µg/ml) (LB-amp-thy-tri) was gently added directly to the cuvette before incubating the sample at 30° C. with shaking for 3 hours. Since the strain now lacks thyA, it is necessary to supplement the media with thymine. Trimethoprim acts as a secondary selector because if the strain still contains an active thyA gene, the trimethoprim is toxic. After that time, the cultures were streaked out onto LB-ampicillin-thymine-trimethoprim agar plates and allowed to incubate at 30° C. overnight. In addition, 250 µl of each culture were sub-cultures into 5 ml of onto LB-ampicillin-thymine-trimethoprim and incubated overnight at 30° C. with shaking.

Gene Deletion

The gene deletion protocol is a two-step process. The first step uses thyA as a selection marker that disrupts the targeted gene. The second step removes thyA from the genome again, following a similar protocol as described previously. For the first step, strain LTS00 is grown overnight in LB-amp-thy-tri and is sub-cultured 1:100 the following morning into 5 ml LB-amp-thy-tri plus 0.2% L-arabinose. These cells are allowed to grow for approximately 6 hours (growth is significantly diminished when lacking thyA) until the $OD_{600}$ reaches 0.6 to 0.8. The cells are then prepared for electroporation as described previously. Prior to electroporation 2 µl of the PCR product containing the thyA gene with homology to the gene to be deleted is added to the sample. Electroporation follows the same protocol as earlier. After electroporation, 1 ml of LB with ampicillin (50 µg/ml) is added, and the cells are allowed to incubate for 3 hours at 30° C. with shaking. After that time, the cultures were streaked out onto LB-ampicillin (150 µg/ml) agar plates and allowed to incubate at 30° C. overnight. In addition, 250 µl of each culture were sub-cultures into 5 ml of onto LB-ampicillin (150 µg/ml) and incubated overnight at 30° C. with shaking.

Figure 6:
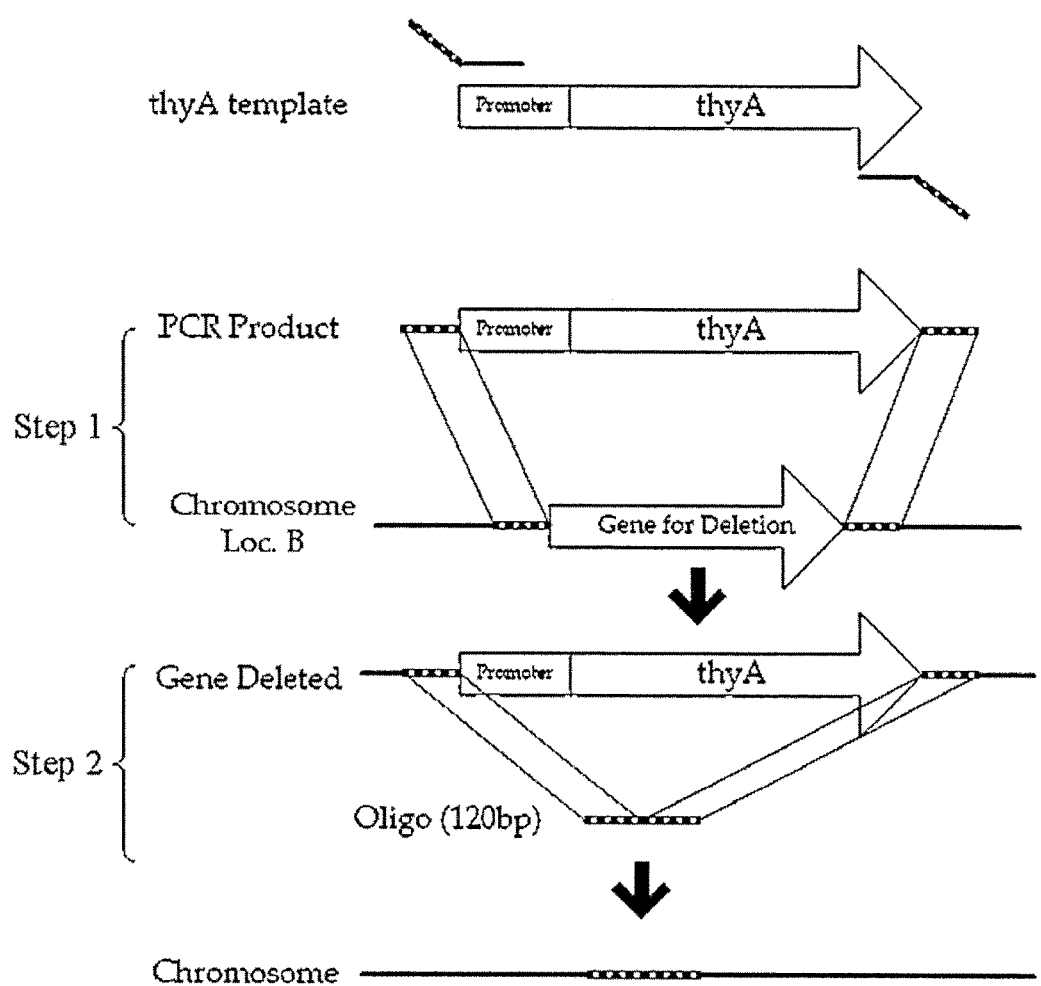
FIG. 6 shows removal of a gene targeted for deletion via a two step process.

FIG. 6 shows the process by which the selection marker is used to cause a gene deletion. Step 1 creates the intermediary thyA+ strain, where the target gene has been deleted but the selection marker remains. At this point, the cell is able to survive on thymine-depleted media. Step 2 removes the thyA marker so that it can be used again for future gene deletions. The protocol is the same as that for the removal of thyA but the 120 bp oligo has homology to the new gene target and removes thyA and its promoter.

Successful deletion of the gene was confirmed via PCR amplification of the deleted region and agarose gel electrophoresis. The amplified regions were also sent for genomic sequencing to further confirm that the homologous recombination event successfully occurred.

TABLE 10

Deletion Fragments.

| Name | Gene Target | Sequence |
|---|---|---|
| thyAdt | thyA | GCAAAATTTCGGGAAGGCGTCTCGAAGAATTTAACGG AGGGTAAAAAAACCGACGCACACGTGTTGCTGTGGGC TGCGACGATATGCCCAGACCATCATGATCACACCCGC GACAATCAT (SEQ ID NO: 4) |
| metHdt | metH | TTTGTTGAATTTTTATTAAATCTGGGTTGAGCGTGTCG GGAGCAAGTGCTGGGGTATGACGCGGACTGATTCACA AATCTGTCACTTTTCCTTACAAC (SEQ ID NO: 5) |
| entFdt | entF | GGCGTACTCTGACACCGACGAATTTTACCCAGTTGCA GGAGGCACACGCGCAACGCTAAACAGGTAAATTAATA TTATTTATAAACCCATAATTAC (SEQ ID NO: 6) |
| tgtdt | tgt | CGCTGGTTTAAAACGTTGGACTGTTTTTCTGACGTAGT GGAGAAAAACCACCTTTGAACGTTGATTAATATTAAT AATGAGGGAAATTTAATGAGCT (SEQ ID NO: 7) |
| rnrdt | rnr | GTGGAGTGACGAAAATCTTCATCAGAGATGACAACGG AGGAACCGAGAAGAAAAAAGTGGCAGAGTGATCAAT ACCCTCTTTAAAAGAAGAGGGTTA (SEQ ID NO: 8) |
| ycaOdt | ycaO | TAAAACCCGTATTATTGCGCGCTTTCCGTACGACTAAA GTGATTTTCGCAGCATTCTGGGCAAAATAAAATCAAA TAGCCTACGCAATGTAGGCTTA (SEQ ID NO: 9) |

These results demonstrate how the separatome can be defined for a chromatographic technique, ion exchange in particular, and can be used to design and construct novel host cells that have certain genes deleted, modified, or inhibited. For example, Table 11 describes ten separate *E. coli* MG1655 derivatives that have one or more gene deletions associated with high affinity host cell proteins. These strains in their current form can be used to express a target recombinant protein and will have enhanced separation efficiency, column capacity in particular, as these proteins are contained in several fractions of high salt concentration.

TABLE 11

*E. coli* Deletion Strains

| Name | Genotype |
|---|---|
| MG1655 | Wild Type: F−, λ−, rph-1 |
| LTS00 | ΔthyA |
| LTS01+ | ΔmetH |
| LTS01 | ΔthyAΔmetH |
| LTS02+ | ΔmetHΔentF |
| LTS02 | ΔthyAΔmetHΔentF |
| LTS03+ | ΔmetHΔentFΔtgt |
| LTS03 | ΔthyAΔmetHΔentFΔtgt |
| LTS04+ | ΔmetHΔentFΔtgtΔrnr |
| LTS04 | ΔthyAΔmetHΔentFΔtgtΔrnr |
| LTS05+ | ΔmetHΔentFΔtgtΔrnrΔycaO |

Table 12 lists high priority genes for DEAF ion exchange media. Future strains of the LTS series of Table 11 will have additional genes identified in Table 12 deleted, modified, or inhibited as the recovery capacity is pushed towards higher values.

TABLE 12

High priority genes of the DEAE separatome, loading pH 7

GeneName rpoC
rpoB
hldD
metH
entF
mukB
tgt
rnr
glgP
recC
ycaO
glnA
ptsI
metE
sucA
hrpA
groL
gatZ
speA
thiI
nusA
tufA
degP
clpB
rapA
metL
ycfD
nagD
ilvA
fusA
cyaA
gldA
dnaK
ygiC
gyrA
glnE
carB
ppsA
degQ
usg
ilvB
thrS
recB
entB
dusA
typA
prs
cysN
atpD
purL The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of purifying a target peptide, polypeptide, or protein, comprising the steps of:
  1) recombinantly or non-recombinantly expressing said target peptide, polypeptide, or protein in a host cell wherein upon chromatographic purification, the chromatographic separation efficiency of said expressed target peptide, polypeptide, or protein is improved in an amount in the range of from about 3% to about 50%, wherein the genome of said host cell:
    a) is a reduced genome,
    b) a modified genome, or
    c) a genome in which expression of genes is reduced or completely inhibited,
  wherein genes that are deleted, modified, or the expression of which is reduced or completely inhibited in said host cell code for peptides, polypeptides, or proteins that impair the chromatographic separation efficiency of said expressed target peptide, polypeptide, or protein,
  wherein deletion, modification, reduction of expression, or complete inhibition of expression of said genes in said host cell improves the chromatographic separation efficiency of said expressed target peptide, polypeptide, or protein in an amount in the range of from about 3% to about 50% compared to the chromatographic separation efficiency of said expressed target peptide, polypeptide, or protein when said genes are not deleted, not modified, or the expression of which is not reduced or completely inhibited in said host cell, respectively, and
  wherein genes that are deleted, modified, or the expression of which is reduced or completely inhibited in the genome of said host cell are identified, scored, and ranked according to chromatographic relevance in adversely affecting said chromatographic separation efficiency of said expressed target peptide, polypeptide, or protein by:
    i) equilibrating an affinity chromatography column comprising an affinity ligand bound to a solid phase, or an adsorption-based, non-affinity chromatography column comprising an adsorption-based, non-affinity chromatography medium, using a mobile loading or eluting phase, or an operational variable;
    ii) in the case where said expressed target peptide, polypeptide, or protein is not secreted from said host cell, fractionating a lysate of said host cell, or
    in the case where said expressed target peptide, polypeptide, or protein is secreted from said host cell, fractionating the culture medium in which said host cell is grown,
    on either of said columns by applying an elution gradient to elute host cell peptide, polypeptide, or protein fractions from said column;
    iii) identifying, quantifying, scoring, and ranking host cell peptides, polypeptides, or proteins in fractions eluted from either of said columns, respectively;

iv) assessing the metabolic role of said host cell peptides, polypeptides, or proteins identified in step iii) that affect column capacity; and v) reducing or modifying the genome of said host cell, or reducing or completely inhibiting expression of genes in said host cell, thereby modifying the proteome of said host cell and increasing the chromatographic separation efficiency of said expressed target peptide, polypeptide, or protein, based on steps iii) and iv) in an amount in the range of from about 3% to about 50% compared to the chromatographic separation efficiency of said expressed target peptide, polypeptide, or protein when said genes are not deleted, not modified, or the expression of which is not inhibited in said host cell, respectively, wherein host cell peptides, polypeptides, and proteins are scored, and ranked in order of importance, in step iii) according to the following equation:

$$importance_i = \sum_j \left[ b_1 \left( \frac{y_{c_j}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i$$

wherein $b_1$=scaling parameter; $y_{c_j}$ and $y_{max}$=concentration of mobile phase eluent in fraction (j) and maximum value, respectively; $h_{i,j}$ and $h_{i,total}$=the amount of protein (i) in fraction (j) and total bound protein (i), respectively; $h_{j,total}$=total amount of protein in fraction (j); $MW_i$=molecular weight of protein (i); $MW_{ref}$=molecular weight of a reference protein within the separatome; $\alpha$=steric factor; and i=protein, wherein:

ratios of y's and h's adopt values between 0 and 1;

a protein that remains bound and requires stringent conditions for elution exhibits a y ratio $$\left( \frac{y_{c_j}}{y_{max}} \right)$$

close to, or equal to, unity;

a protein that emerges as a tight peak has an h ratio $$\left( \frac{h_{i,j}}{h_{i,total}} \right)$$

close to unity and a j ratio $$\left( \frac{h_{i,j}}{h_{j,total}} \right)$$

close to unity if it constitutes the majority of fraction (j);

a non-zero $\alpha$ between 0 and 1 indicates steric effects; and wherein the quantitative ranking for a protein is calculated by multiplying $$b_1 \times \left( \frac{y_{c_j}}{y_{max}} \right) \times \left( \frac{h_{i,j}}{h_{i,total}} \right) \times \left( \frac{h_{i,j}}{h_{j,total}} \right) \times \left( \frac{MW_i}{MW_{ref}} \right)^\alpha,$$

and summing the product for each fraction (j) where (i) is present;

2) in the case where said expressed target peptide, polypeptide, or protein is not secreted from said host cell, preparing a lysate of said host cell containing said expressed target peptide, polypeptide, or protein, producing an initial expressed target peptide-, polypeptide-, or protein-containing mixture; or 3) in the case where said expressed target peptide, polypeptide, or protein is secreted from said host cell, harvesting culture medium in which said host cell is grown, containing said expressed target peptide, polypeptide, or protein, thereby obtaining an initial expressed target peptide-, polypeptide-, or protein-containing mixture;

4) chromatographing said initial expressed target peptide-, polypeptide-, or protein-containing mixture of step 2) or step 3) using an affinity chromatography column comprising an affinity ligand bound to a solid phase, or an adsorption-based, non-affinity chromatography medium-containing column, and collecting elution fractions, thereby obtaining one or more fractions containing an enriched amount of said expressed target peptide, polypeptide, or protein relative to other peptides, polypeptides, or proteins in said fraction compared to the amount of said expressed target peptide, polypeptide, or protein relative to other peptides, polypeptides, or proteins in said initial expressed target peptide-, polypeptide-, or protein-containing mixture; and 5) further chromatographing an enriched fraction of step 4) to obtain said expressed target peptide, polypeptide, or protein in a desired degree of purity.

2. The method of claim 1, further comprising recovering purified expressed target peptide, polypeptide, or protein.

3. The method of claim 1, wherein said host cell is selected from the group consisting of a bacterium, a fungus, a mammalian cell, an insect cell, a plant cell, and a protozoal cell.

4. The method of claim 3, wherein said bacterium is selected from *E. coli, L. lactis, B. subtilis, B. licheniformis, B. amyloliquefaciens, P. fluorescens*, and *C. glutamicum*; said fungus is a yeast selected from *S. cerevisiae, K. pastoris*, and *P. methanolica*; said mammalian cell is selected from a CHO cell, a HEK cell, a mouse myeloma cell, a BHK cell, and a human retinal cell; said insect cell is selected from an *S. frugiperda* cell, a *T. ni* cell, and a *D. melanogaster* cell; said plant cell is selected from a tobacco, alfalfa, rice, tomato, soybean, and an algal cell; and said protozoal cell is a *L. tarentolae* cell.

5. The method of claim 1, where said adsorption-based, non-affinity chromatography column is an ion exchange chromatography column.

6. The method of claim 1, wherein said recombinantly expressed expressed target peptide, polypeptide, or protein is an endogenous peptide, polypeptide, or protein of said host cell, or is a heterologous peptide, polypeptide, or protein.

7. The method of claim 6, wherein:

said recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and said recombinantly expressed heterologous peptide, polypeptide, or protein is selected from the group consisting of an enzyme and a therapeutic peptide, polypeptide, or protein.

8. The method of claim 7, wherein:
said recombinantly expressed heterologous enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, lung surfactant protein, serum albumin, tissue plasminogen activator, and tumor necrosis factor.

9. The method of claim 1, wherein said non-recombinantly expressed target peptide, polypeptide, or protein is an endogenous peptide, polypeptide, or protein of said host cell.

10. The method of claim 9, wherein said non-recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

11. A method of enriching the amount of a target peptide, polypeptide, or protein relative to other peptides, polypeptides, or proteins present in an initial protein mixture comprising said target peptide, polypeptide, or protein, comprising the steps of:
1) recombinantly or non-recombinantly expressing said target peptide, polypeptide, or protein in a host cell wherein upon chromatographic purification, the chromatographic separation efficiency of said target peptide, polypeptide, or protein is improved in an amount in the range of from about 3% to about 50%,
wherein the genome of said host cell:
a) is a reduced genome,
b) a modified genome, or
c) a genome in which expression of genes is reduced or completely inhibited,
wherein genes that are deleted, modified, or the expression of which is reduced or completely inhibited in said host cell code for peptides, polypeptides, or proteins that impair the chromatographic separation efficiency of said target peptide, polypeptide, or protein,
wherein deletion, modification, reduction of expression, or complete inhibition of expression of said genes in said host cell improves the chromatographic separation efficiency of said target peptide, polypeptide, or protein in an amount in the range of from about 3% to about 50% compared to the chromatographic separation efficiency of said target peptide, polypeptide, or protein when said genes are not deleted, not modified, or the expression of which is not reduced or completely inhibited in said host cell, respectively, and
wherein genes that are deleted, modified, or the expression of which is reduced or completely inhibited in the genome of said host cell are identified, scored, and ranked according to chromatographic relevance in adversely affecting said chromatographic separation efficiency of said target peptide, polypeptide, or protein by:

i) equilibrating an affinity chromatography column comprising an affinity ligand bound to a solid phase, or an adsorption-based, non-affinity chromatography column comprising an adsorption-based, non-affinity chromatography medium, using a mobile loading or eluting phase, or an operational variable;
ii) in the case where said target peptide, polypeptide, or protein is not secreted from said host cell, fractionating a lysate of said host cell, or
in the case where said target peptide, polypeptide, or protein is secreted from said host cell, fractionating the culture medium in which said host cell is grown,
on either of said columns by applying an elution gradient to elute host cell peptide, polypeptide, or protein fractions from said column;
iii) identifying, quantifying, scoring, and ranking host cell peptides, polypeptides, or proteins in fractions eluted from either of said columns, respectively;
iv) assessing the metabolic role of said host cell peptides, polypeptides, or proteins identified in step iii) that affect column capacity; and
v) reducing or modifying the genome of said host cell, or reducing or completely inhibiting expression of genes in said host cell, thereby modifying the proteome of said host cell and increasing the chromatographic separation efficiency of said target peptide, polypeptide, or protein based on steps iii) and iv) in an amount in the range of from about 3% to about 50% compared to the chromatographic separation efficiency of said target peptide, polypeptide, or protein expressed in said host cell when said genes are not deleted, not modified, or the expression of which is not inhibited in said host cell, respectively,
wherein host cell peptides, polypeptides, and proteins are scored, and ranked in order of importance, in step iii) according to the following equation:

$$importance_i = \sum_j \left[ b_1 \left( \frac{y_{c_j}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^a \right]_i$$

wherein $b_1$=scaling parameter; $y_{c_j}$ and $y_{max}$=concentration of mobile phase eluent in fraction (j) and maximum value, respectively; $h_{i,j}$ and $h_{i,total}$=the amount of protein (i) in fraction (j) and total bound protein (i), respectively; $h_{j,total}$=total amount of protein in fraction (j); $MW_i$=molecular weight of protein (i); $MW_{ref}$=molecular weight of a reference protein within the separatome; a=steric factor; and i=protein, wherein:
ratios of y's and h's adopt values between 0 and 1;
a protein that remains bound and requires stringent conditions for elution exhibits a y ratio $$\left( \frac{y_{c_j}}{y_{max}} \right)$$

close to, or equal to, unity;
a protein that emerges as a tight peak has an h ratio $$\left( \frac{h_{i,j}}{h_{i,total}} \right)$$

close to unity and a j ratio $$\left(\frac{h_{i,j}}{h_{j,total}}\right)$$

close to unity if it constitutes the majority of fraction (j);

a non-zero α between 0 and 1 indicates steric effects; and wherein the quantitative ranking for a protein is calculated by multiplying $$b_1 \times \left(\frac{y_{c_j}}{y_{max}}\right) \times \left(\frac{h_{i,j}}{h_{i,total}}\right) \times \left(\frac{h_{i,j}}{h_{j,total}}\right) \times \left(\frac{MW_i}{MW_{ref}}\right)^\alpha,$$

and summing the product for each fraction (j) where (i) is present;

2) in the case where said target peptide, polypeptide, or protein is not secreted from said host cell, preparing a lysate of said host cell containing said target peptide, polypeptide, or protein, producing an initial target peptide-, polypeptide-, or protein-containing mixture; or 3) in the case where said target peptide, polypeptide, or protein is secreted from said host cell, harvesting culture medium in which said host cell is grown, containing said target peptide, polypeptide, or protein, thereby obtaining an initial target peptide-, polypeptide-, or protein-containing mixture; and 4) chromatographing said initial target peptide-, polypeptide-, or protein-containing mixture of step 2) or step 3) using an affinity chromatography column comprising an affinity ligand bound to a solid phase, or an adsorption-based, non-affinity chromatography medium-containing column, and collecting elution fractions, thereby obtaining one or more fractions containing an enriched amount of said target peptide, polypeptide, or protein relative to other peptides, polypeptides, or proteins in said fraction compared to the amount of said target peptide, polypeptide, or protein relative to other peptides, polypeptides, or proteins in said initial target peptide-, polypeptide-, or protein-containing mixture.

12. The method of claim 11, further comprising chromatographing an enriched fraction of step 4) to obtain said target peptide, polypeptide, or protein in a desired degree of purity.

13. The method of claim 12, further comprising recovering said target peptide, polypeptide, or protein.

14. The method of claim 11, wherein said host cell is selected from the group consisting of a bacterium, a fungus, a mammalian cell, an insect cell, a plant cell, and a protozoal cell.

15. The method of claim 14, wherein said bacterium is selected from *E. coli, L. lactis, B. subtilis, B. licheniformis, B. amyloliquefaciens, P. fluorescens*, and *C. glutamicum*; said fungus is a yeast selected from *S. cerevisiae, K. pastoris*, and *P. methanolica*; said mammalian cell is selected from a CHO cell, a HEK cell, a mouse myeloma cell, a BHK cell, and a human retinal cell; said insect cell is selected from an *S. frugiperda* cell, a *T. ni* cell, and a *D. melanogaster* cell; said plant cell is selected from a tobacco, alfalfa, rice, tomato, soybean, and an algal cell; and said protozoal cell is a *L. tarentolae* cell.

16. The method of claim 11, where said adsorption-based, non-affinity chromatography column is an ion exchange chromatography column.

17. The method of claim 11, wherein said recombinantly expressed target peptide, polypeptide, or protein is an endogenous peptide, polypeptide, or protein of said host cell, or is a heterologous peptide, polypeptide, or protein.

18. The method of claim 17, wherein:
said recombinantly expressed endogenous target peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed heterologous target peptide, polypeptide, or protein is selected from the group consisting of an enzyme and a therapeutic peptide, polypeptide, or protein.

19. The method of claim 18, wherein:
said recombinantly expressed heterologous enzyme is selected from the group consisting of a nuclease, a ligase, a polymerase, an RNA- or DNA-modifying enzyme, a carbohydrate-modifying enzyme, an isomerase, a proteolytic enzyme, and a lipolytic enzyme, and
said recombinantly expressed therapeutic peptide, polypeptide, or protein is selected from the group consisting of antibody, an antibody fragment, a vaccine, an enzyme, a growth factor, a blood clotting factor, a hormone, a nerve factor, an interferon, an interleukin, lung surfactant protein, serum albumin, tissue plasminogen activator, and tumor necrosis factor.

20. The method of claim 11, wherein said non-recombinantly expressed target peptide, polypeptide, or protein is an endogenous peptide, polypeptide, or protein of said host cell.

21. The method of claim 20, wherein said non-recombinantly expressed endogenous peptide, polypeptide, or protein is selected from the group consisting of a nuclease, a ligase, a polymerase, an RNA- or DNA-modifying enzyme, a carbohydrate-modifying enzyme, an isomerase, a proteolytic enzyme, and a lipolytic enzyme.

22. A method of preparing a pharmaceutical or veterinary composition comprising a recombinant therapeutic peptide, polypeptide, or protein, comprising the steps of:
1) expressing said recombinant therapeutic peptide, polypeptide, or protein in a host cell wherein upon chromatographic purification, the chromatographic separation efficiency of said recombinant therapeutic peptide, polypeptide, or protein expressed in said host cell is improved in an amount in the range of from about 3% to about 50%,
wherein the genome of said host cell:
a) is a reduced genome,
b) a modified genome, or
c) a genome in which expression of genes is reduced or completely inhibited,
wherein genes that are deleted, modified, or the expression of which is reduced or completely inhibited in said host cell code for peptides, polypeptides, or proteins that impair the chromatographic separation efficiency of said recombinant therapeutic peptide, polypeptide, or protein expressed in said host cell,
wherein deletion, modification, reduction of expression, or complete inhibition of expression of said genes in said host cell improves the chromatographic separation efficiency of said recombinant therapeutic peptide, polypeptide, or protein expressed in said host cell in an amount in the range of from about 3% to about 50% compared to the chromatographic separation efficiency of said recombinant therapeutic peptide, polypeptide, or protein expressed in said host cell when said genes are not deleted, not modified, or the expression of which is not reduced or completely inhibited in said host cell, respectively, and wherein genes that are deleted, modified, or the expression of which is reduced or completely inhibited, in the genome of said host cell are identified, scored, and ranked according to chromatographic relevance in adversely affecting said chromatographic separation efficiency of said recombinant therapeutic peptide, polypeptide, or protein by:

i) equilibrating an affinity chromatography column comprising an affinity ligand bound to a solid phase, or an adsorption-based, non-affinity chromatography column comprising an adsorption-based, non-affinity chromatography medium, using a mobile loading or eluting phase, or an operational variable;

ii) in the case where said recombinant therapeutic peptide, polypeptide, or protein is not secreted from said host cell, fractionating a lysate of said host cell, or
in the case where said recombinant therapeutic peptide, polypeptide, or protein is secreted from said host cell, fractionating the culture medium in which said host cell is grown,
on either of said columns by applying an elution gradient to elute host cell peptide, polypeptide, or protein fractions from said column;

iii) identifying, quantifying, scoring, and ranking host cell peptides, polypeptides, or proteins in fractions eluted from either of said columns;

iv) assessing the metabolic role of said host cell peptides, polypeptides, or proteins identified in step iii) that affect column capacity; and v) reducing or modifying the genome of said host cell, or reducing or completely inhibiting expression of genes in said host cell, thereby modifying the proteome of said host cell and increasing the chromatographic separation efficiency of said recombinant therapeutic peptide, polypeptide, or protein, based on steps iii) and iv) in an amount in the range of from about 3% to about 50% compared to the chromatographic separation efficiency of said recombinant therapeutic peptide, polypeptide, or protein expressed in said host cell when said genes are not deleted, not modified, or the expression of which is not inhibited in said host cell, respectively, wherein host cell peptides, polypeptides, and proteins are scored, and ranked in order of importance, in step iii) according to the following equation:

$$\text{importance}_i = \sum_j \left[ b_1 \left( \frac{y_{c_j}}{y_{max}} \right) \left( \frac{h_{i,j}}{h_{i,total}} \right) \left( \frac{h_{i,j}}{h_{j,total}} \right) \left( \frac{MW_i}{MW_{ref}} \right)^\alpha \right]_i$$

wherein $b_1$=scaling parameter; $y_{c_j}$ and $y_{max}$=concentration of mobile phase eluent in fraction (j) and maximum value, respectively; $h_{i,j}$ and $h_{i,total}$=the amount of protein (i) in fraction (j) and total bound protein (i), respectively; $h_{j,total}$=total amount of protein in fraction (j); $MW_i$=molecular weight of protein (i); $MW_{ref}$=molecular weight of a reference protein within the separatome; $\alpha$=steric factor; and i=protein, wherein:

ratios of y's and h's adopt values between 0 and 1;
a protein that remains bound and requires stringent conditions for elution exhibits a y ratio $$\left( \frac{y_{c_j}}{y_{max}} \right)$$

close to, or equal to, unity;
a protein that emerges as a tight peak has an h ratio $$\left( \frac{h_{i,j}}{h_{i,total}} \right)$$

close to unity and a j ratio $$\left( \frac{h_{i,j}}{h_{j,total}} \right)$$

close to unity if it constitutes the majority of fraction (j);
a non-zero α between 0 and 1 indicates steric effects; and
wherein the quantitative ranking for a protein is calculated by multiplying $$b_1 \times \left( \frac{y_{c_j}}{y_{max}} \right) \times \left( \frac{h_{i,j}}{h_{i,total}} \right) \times \left( \frac{h_{i,j}}{h_{j,total}} \right) \times \left( \frac{MW_i}{MW_{ref}} \right)^\alpha,$$

and summing the product for each fraction (j) where (i) is present;

2) in the case where said recombinant therapeutic peptide, polypeptide, or protein is not secreted from said host cell, preparing a lysate of said host cell containing said recombinant therapeutic peptide, polypeptide, or protein, producing an initial recombinant therapeutic peptide-, polypeptide-, or protein-containing mixture; or 3) in the case where said recombinant therapeutic peptide, polypeptide, or protein is secreted from said host cell, harvesting culture medium in which said host cell is grown, containing said recombinant therapeutic peptide, polypeptide, or protein, thereby obtaining an initial recombinant therapeutic peptide-, polypeptide-, or protein-containing mixture;

4) chromatographing said initial recombinant therapeutic peptide-, polypeptide-, or protein-containing mixture of step 2) or step 3) using an affinity chromatography column comprising an affinity ligand bound to a solid phase, or an adsorption-based, non-affinity chromatography medium-containing column, and collecting elution fractions, thereby obtaining one or more fractions containing an enriched amount of said recombinant therapeutic peptide, polypeptide, or protein relative to other peptides, polypeptides, or proteins in said fraction compared to the amount of said recombinant therapeutic peptide, polypeptide, or protein relative to other peptides, polypeptides, or proteins in said initial recombinant peptide-, polypeptide-, or protein-containing mixture;

5) further chromatographing an enriched fraction of step 4) to obtain said recombinant therapeutic peptide, polypeptide, or protein in a desired degree of purity;

6) recovering purified recombinant therapeutic peptide, polypeptide, or protein; and 7) formulating said purified recombinant therapeutic peptide, polypeptide, or protein of step 6) with a pharmaceutically or veterinarily acceptable carrier, diluent, or excipient to produce a pharmaceutical or veterinary composition, respectively.

23. The method of claim 22, wherein said host cell is selected from the group consisting of a bacterium, a fungus, a mammalian cell, an insect cell, a plant cell, and a protozoal cell.

24. The method of claim 23, wherein said bacterium is selected from *E. coli, L. lactis, B. subtilis, B. licheniformis, B. amyloliquefaciens, P. fluorescens,* and *C. glutamicum*; said fungus is a yeast selected from *S. cerevisiae, K. pastoris,* and *P. methanolica*; said mammalian cell is selected from a CHO cell, a HEK cell, a mouse myeloma cell, a BHK cell, and a human retinal cell; said insect cell is selected from an *S. frugiperda* cell, a *T. ni* cell, and a *D. melanogaster* cell; said plant cell is selected from a tobacco, alfalfa, rice, tomato, soybean, and an algal cell; and said protozoal cell is a *L. tarentolae* cell.

25. The method of claim 22, wherein said adsorption-based, non-affinity chromatography column is an ion exchange chromatography column.

26. The method of claim 22, wherein said recombinant therapeutic peptide, polypeptide, or protein is selected from the group consisting of antibody, an antibody fragment, a vaccine, a growth factor, a blood clotting factor, a hormone, a nerve factor, an interferon, an interleukin, lung surfactant protein, serum albumin, tissue plasminogen activator, and tumor necrosis factor.

27. The method of claim 22, wherein said recombinant therapeutic peptide, polypeptide, or protein is an enzyme.

* * * * *

SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Synthesized 6 His tag

<400> SEQUENCE: 1

His His His His His His
1               5

<210> SEQ ID NO 2
<211> LENGTH: 52
<212> TYPE: DNA
<213> ORGANISM: Artificial Sequence
<220> FEATURE:
<223> OTHER INFORMATION: PCR Primer

<400> SEQUENCE: 2
gccaagcttg tggcatcatc atccgcatat gagtaaagga gaagaacttt tc       52

<210> SEQ ID NO 3
<211> LENGTH: 24
<212> TYPE: DNA
<213> ORGANISM: Artificial Sequence
<220> FEATURE:
<223> OTHER INFORMATION: PCR Primer

<400> SEQUENCE: 3
ttggaattca ttatttgtag agct                                      24

<210> SEQ ID NO 4
<211> LENGTH: 120
<212> TYPE: DNA
<213> ORGANISM: Artificial Sequence
<220> FEATURE:
<223> OTHER INFORMATION: thyA gene deletion fragment

<400> SEQUENCE: 4
gcaaaatttc gggaaggcgt ctcgaagaat ttaacggagg gtaaaaaaac cgacgcacac    60
gtgttgctgt gggctgcgac gatatgccca gaccatcatg atcacacccg cgacaatcat   120

<210> SEQ ID NO 5
<211> LENGTH: 98
<212> TYPE: DNA
<213> ORGANISM: Artificial Sequence
<220> FEATURE:
<223> OTHER INFORMATION: metH gene deletion fragment

<400> SEQUENCE: 5
tttgttgaat ttttattaaa tctgggttga gcgtgtcggg agcaagtgct ggggtatgac    60
gcggactgat tcacaaatct gtcactttc cttacaac                            98

<210> SEQ ID NO 6
<211> LENGTH: 96
<212> TYPE: DNA
<213> ORGANISM: Artificial Sequence
<220> FEATURE:
<223> OTHER INFORMATION: entF gene deletion fragment

<400> SEQUENCE: 6
ggcgtactct gacaccgacg aattttaccc agttgcagga ggcacacgcg caacgctaaa    60

```
caggtaaatt aatattattt ataaacccat aattac                            96

<210> SEQ ID NO 7
<211> LENGTH: 97
<212> TYPE: DNA
<213> ORGANISM: Artificial Sequence
<220> FEATURE:
<223> OTHER INFORMATION: tgt gene deletion fragment

<400> SEQUENCE: 7
cgctggttta aaacgttgga ctgtttttct gacgtagtgg agaaaaacca cctttgaacg    60
ttgattaata ttaataatga gggaaattta atgagct                            97

<210> SEQ ID NO 8
<211> LENGTH: 97
<212> TYPE: DNA
<213> ORGANISM: Artificial Sequence
<220> FEATURE:
<223> OTHER INFORMATION: rnr gene deletion fragment

<400> SEQUENCE: 8
gtggagtgac gaaatcttc atcagagatg acaacggagg aaccgagaag aaaaaagtgg    60
cagagtgatc aataccctct ttaaaagaag agggtta                            97

<210> SEQ ID NO 9
<211> LENGTH: 97
<212> TYPE: DNA
<213> ORGANISM: Artificial Sequence
<220> FEATURE:
<223> OTHER INFORMATION: ycaO gene deletion fragment

<400> SEQUENCE: 9
taaaacccgt attattgcgc gctttccgta cgactaaagt gattttcgca gcattctggg    60
caaaataaaa tcaaatagcc tacgcaatgt aggctta                            97
```